(12) United States Patent
Vandervalk et al.

(10) Patent No.: US 8,994,933 B2
(45) Date of Patent: Mar. 31, 2015

(54) APPARATUS AND METHOD FOR CHARACTERIZING A REPLICA TAPE

(71) Applicant: DeFelsko Corporation, Ogdensburg, NY (US)

(72) Inventors: Leon Vandervalk, Brockville (CA); Robert V. Stachnik, Newark, DE (US); James Edward Davis, Wilmington, DE (US)

(73) Assignee: DeFelsko Corporation, Ogdensburg, NY (US)

( * ) Notice: Subject to any disclaimer, the term of this patent is extended or adjusted under 35 U.S.C. 154(b) by 0 days.

(21) Appl. No.: 14/151,066

(22) Filed: Jan. 9, 2014

(65) Prior Publication Data

US 2014/0192346 A1   Jul. 10, 2014

Related U.S. Application Data

(60) Provisional application No. 61/750,521, filed on Jan. 9, 2013.

(51) Int. Cl.
   *G01N 21/00*   (2006.01)
   *G01B 11/06*   (2006.01)

(52) U.S. Cl.
   CPC .................................... *G01B 11/06* (2013.01)
   USPC ......................................................... 356/72

(58) Field of Classification Search
   CPC ... H01J 37/32935; G01N 21/64; G01N 21/68; G01N 2015/1037; G01J 3/02
   USPC .......................................................... 356/72
   See application file for complete search history.

(56) References Cited

U.S. PATENT DOCUMENTS

| 5,688,695 A | 11/1997 | Kramer |
| 8,411,272 B2 | 4/2013 | Hansen |
| 2003/0222215 A1 | 12/2003 | De Robillard et al. |
| 2012/0261256 A1 | 10/2012 | Chang et al. |

FOREIGN PATENT DOCUMENTS

| EP | 2151679 A3 | 8/2003 |
| EP | 1403613 B1 | 3/2004 |

OTHER PUBLICATIONS

Notification of Transmittal of the International Search Report and the Written Opinion of the International Searching Authority mailed on May 12, 2014, in the corresponding International Application No. PCT/US2014/010802. (12 pages).

*Primary Examiner* — Tarifur Chowdhury
*Assistant Examiner* — Md Rahman
(74) *Attorney, Agent, or Firm* — Buchanan Ingersoll & Rooney PC

(57) ABSTRACT

An apparatus and method are provided for characterizing a replica tape which has been embossed, compressed or cast on a surface of a material to be measured to replicate that surface. The replica tape is secured between first and second holding components such that a compressible surface of the replica tape is secured against the first holding component. A light source transmits light through the second holding component, the replica tape and the first holding component. An image sensor measures intensity of the light respectively transmitted through at least two measurement points of the compressible surface of the replica tape. A processing unit converts the measured light intensity transmitted through the at least two measurement points into at least two data values each respectively relating to a measurement statistic of the replica tape at a corresponding one of the at least two measurement points, respectively.

41 Claims, 15 Drawing Sheets

201- Image Sensor
202- Light Source
203- Thickness Sensor
204- Tape
205- Image Processor
206- User Interface Processor
207- Display No Tape Intensity Map Uncompressed Tape Intensity Map FIG. 10
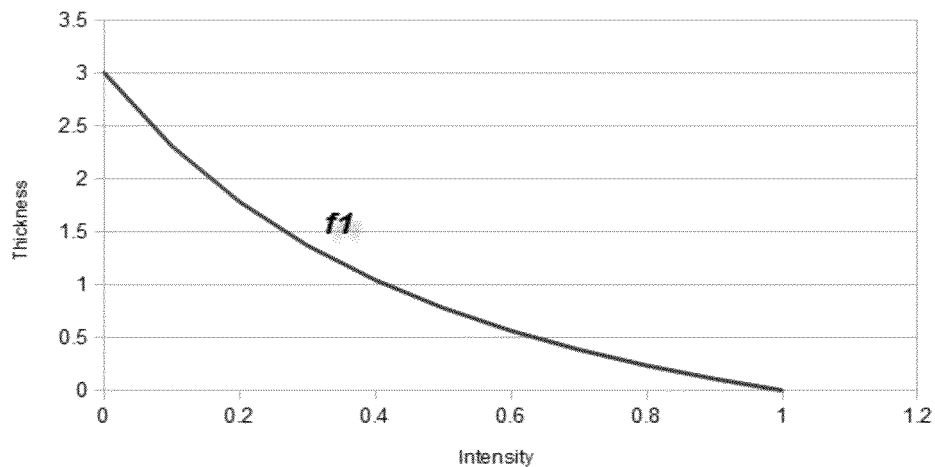
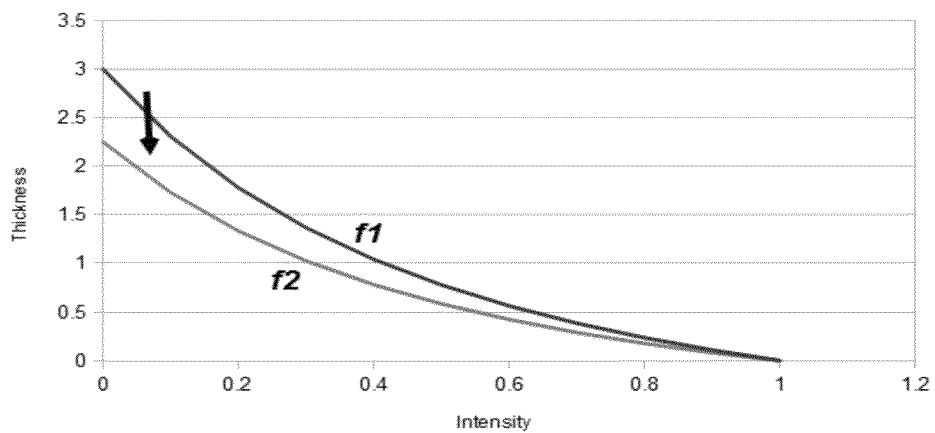
Intensity vs. Thickness After Scaling
FIG. 11

APPARATUS AND METHOD FOR CHARACTERIZING A REPLICA TAPE

RELATED APPLICATION

The present application claims priority to U.S. Provisional Application No. 61/750,521, filed on Jan. 9, 2013.

FIELD

The present disclosure relates to a method and apparatus for characterizing a replica tape which has been embossed or compressed to represent an original surface of a material. More particularly, the present disclosure relates to a method and apparatus for characterizing such an embossed or compressed replica tape by transmitting light through the replica tape for measurements of dimensions of structures and statistics thereof, and optionally generating and displaying images of the characterized surface. In addition, the present disclosure relates to a method and apparatus for characterizing such an embossed or compressed replica tape by measuring the displacement of the replica tape thickness to find a maximum peak to valley distance of a surface, using means such as a spring micrometer or eddy current sensor, for example.

BACKGROUND

In the field of Non-Destructive Testing surface analysis, known techniques include visual inspection, liquid penetrant, and magnetic particle inspection. In addition, microscopy techniques such as confocal, interferometric, scanning electron microscopy (SEM) and mechanical surface profile instruments such as one- and two-dimensioned styles based instruments are known techniques to determine a surface a profile. Within the class of visual inspection techniques, surface replication may be used to aid in the remote inspection of materials. Known surface replication techniques involve the transfer of a surface profile to a media such as a replica tape for indirect examination using microscopy. Known replica tape uses a cellulose acetate film to transfer surface profiling for imaging microstructures with standard microscopy techniques. However, this technique is not used for surface profiling but rather typically as a means to ascertain image crack formation or creep damage of components.

Other known methods of surface transfer to a replicating media include replication putty, shape memory polymer, as well as casting techniques using two-part silicon rubbers and methacrylate. The resulting replica is analyzed using a number of techniques including interferometric, scanning electron microscopy (SEM), and confocal microscopy. One or two-dimensional mechanical surface profile instruments can also be used on the replica media, such as drag stylus or needle type surface profile gages.

It is known to use replica tape to characterize a surface. Method C of ASTM D4417 describes the process for measuring the peak to valley distance of a surface, such as abrasive blasted surfaces on metal bridges and ships, for example. The character of the blasted surface is predictive of paint adherence. If the peak to valley distance is too small, the surface lacks sufficient "tooth" to anchor the paint. If the peak to valley distance is too large, the high peaks may protrude through the paint to become foci for corrosion.

PRESS-O-FILM®, which is an example of a commercially available replica tape, includes a non-compressible 50 µm (2 mil) polyester backing and a compressible layer of foam. The backing is attached to an adhesive backed paper carrier. The carrier has an approximately 8 mm diameter opening exposing the polyester and foam below which is embossed or compressed against the surface to be characterized causing the foam to conform to the surface. The thickness of the replica tape is then measured with a spring loaded micrometer, and the thickness of the polyester backing is subtracted to indicate the peak to valley distance of the original surface. However, the micrometer is not capable of providing other measurements, such as the peaks per unit area, the mean peak area, or developed surface area. These additional statistics may be useful in further predicting paint adherence and longevity.

Replica tape provides a permanent record of the surface. Some micrometers can also store the thickness reading of the replica tape to provide a permanent record of the peak to valley measurement. Such micrometers, however, do not provide additional measures of the surface.

Replica tape is particularly useful for measurements on curved surfaces that are difficult to measure directly with stylus instruments or interferometric laser scanning or optical focal distance measuring devices.

The use of imaging techniques in conjunction with replica media is known. Both reflective and backlit techniques have been employed to analyze surfaces. Commercially available metalized replica tape is useful for scanning electron microscope characterization of the surface. Metalized replica tape is also useful for interferometric characterization of the surface, for example, when the original surface is insufficiently reflective. However, these techniques are neither low cost nor portable.

Most materials exhibit absorbance to radiation at particular wavelengths. This is known as the Beer-Lambert law. It is known that a mapping of thickness to absorbance can yield a 3D image. However, known surface analysis techniques do not involve deriving a calibrated thickness mapping of such an image. For example, U.S. 2003/0222215 discloses a technique of determining the thickness of a thin layer coated on a surface of a sample by taking a picture of the section to be examined to obtain a digital image of that section. An intensity profile in the thickness direction of the thin layer is extracted from the digital image and is then analyzed based on characteristics of the intensity profile that are independent from properties of the sample, such as sample thickness, a radius of curvature of the thin layer in a thickness direction of the thin layer, and a tilt angle introduced during the preparation of the sample. However, U.S. 2003/0222215 involves the use of expensive radiation equipment such as an x-ray machine in order to emit electron radiation to ascertain an intensity profile in the thickness direction of the thin layer at an atomic level. Furthermore, U.S. 2003/0222215 does not provide for any mechanism for performing in situ calibration adjustments of the profile based on the corresponding thickness measurements.

Exemplary embodiments of the present disclosure provide an apparatus and method to derive a thickness profile of a replication media by using an independent thickness measurement means to calibrate a characteristic intensity profile. The apparatus is specifically constructed to derive a calibrated thickness profile of a replication media such as a replica tape, for example.

SUMMARY

An exemplary embodiment of the present disclosure provides an apparatus for characterizing a replica tape which has been embossed, compressed or cast on a surface of a material. The replica tape includes a first surface and an opposing second surface replicating the surface of the material on which the replica tape was embossed, compressed or cast. The second surface of the replica tape has a plurality of measurement points extending along a first direction substantially perpendicular to a thickness of the replica tape extending in a second direction between the first and second surfaces of the replica tap. The exemplary apparatus includes a first holding component having opposing first and second surfaces in the second direction, where the first surface of the first holding component is configured to support the second surface of the replica tape thereon. The exemplary apparatus also includes a second holding component having opposing first and second surfaces in the second direction, where the second holding component is configured to be pressed against the first surface of the replica tape to secure the replica tape between the first surface of the first holding component and the second surface of the second holding component. In addition, the exemplary apparatus includes a light source arranged a first distance from the first surface of the second holding component and configured to transmit light in the second direction through the first and second surfaces of the second holding component, the first and second surfaces of the replica tape, and the first and second surfaces of the first holding component. The exemplary apparatus also includes an image sensor arranged a second distance from the second surface of the first holding component and configured to measure an intensity of the light respectively transmitted through at least two of the plurality of measurement points of the second surface of the replica tape. Furthermore, the exemplary apparatus includes a processing unit configured to receive the measured intensity of the light transmitted through the at least two of the plurality measurement points and convert the measured light intensity at the at least two measurement points into at least two data values each respectively relating to a measurement statistic of the replica tape at a corresponding one of the at least two measurement points, respectively.

According to an exemplary embodiment, the image sensor is configured to measure the intensity of the light respectively transmitted through the at least two measurement points by measuring an amplitude of a corresponding wavelength of the light transmitted through the at least two measurement points, respectively.

According to an exemplary embodiment, the light source is configured to transmit light having a wavelength of 200 to 1500 nm.

According to an exemplary embodiment, the light source is configured to transmit infrared light.

According to an exemplary embodiment, the image sensor includes a digital camera having a Bayer filter, and the infrared light transmitted by the light source bypasses the Bayer filter of the digital camera.

According to an exemplary embodiment, the apparatus includes a band pass filter arranged between the second surface of the first holding component and the image sensor, the band pass filter being configured to pass only infrared light to the image sensor.

According to an exemplary embodiment, the apparatus includes an eddy current sensor arranged on the second surface of the first holding component, and a conductive element attached to at least one point on a periphery of the second holding component between the first and second surfaces of the second holding component. The second holding component and the conductive element attached to the second holding component are movable in the second direction. The eddy current sensor is configured to measure a height of the conductive element above the first holding component. The processing unit is configured to measure a height of the second holding component based on the measured height of the conductive element, and convert the measured height of the second holding component to a peak to valley thickness according to the measured height of the second holding component.

According to an exemplary embodiment, the replica tape includes a transparent backing attached to the first surface of the replica tape. The second holding component is configured to be pressed against the transparent backing to secure the replica tape between the first surface of the first holding component and the second surface of the second holding component.

According to an exemplary embodiment, the backing is composed of one of polyester and nylon.

According to an exemplary embodiment, the apparatus includes an eddy current sensor arranged on the second surface of the first holding component, and a conductive element attached to at least one point on a periphery of the second holding component between the first and second surfaces of the second holding component. The second holding component and the conductive element attached to the second holding component are movable in the second direction. The eddy current sensor is configured to measure a height of the conductive element above the first holding component. The processing unit is configured to measure a height of the second holding component based on the measured height of the conductive element, and convert the measured height of the second holding component to a peak to valley thickness by subtracting the measured height of the second holding component from a thickness of the transparent backing.

According to an exemplary embodiment, the apparatus includes an eddy current sensor arranged on the second surface of the first holding component. The second holding component is composed of a conductive material and is moveable in the second direction. The eddy current sensor is configured to measure a height of the second holding component above the first holding component. The processing unit is configured to convert the measured height of the second holding component to a peak to valley thickness by subtracting the measured height of the second holding component from a thickness of the transparent backing.

According to an exemplary embodiment, the apparatus includes an eddy current sensor arranged on the second surface of the first holding component. The second holding component is composed of a conductive material and is moveable in the second direction. The eddy current sensor is configured to measure a height of the second holding component above the first holding component. The processing unit is configured to convert the measured height of the second holding component to a peak to valley thickness according to the measured height of the second holding component.

According to an exemplary embodiment, the apparatus includes a first spring configured to apply a first predetermined force to the first surface of the second holding component to keep pressure between the second holding component and the replica tape constant, regardless of operator input.

According to an exemplary embodiment, the apparatus includes a second spring surrounding the second holding component, and a first ring surrounding the second holding component and having an inner groove configured to accommodate and engage the second spring between the first and second surfaces of the second holding component, and an outer tapered surface. In addition, the apparatus includes a pair of buttons respectively disposed on opposite sides of the second holding component and each including an inner tapered surface matching a contour of the outer tapered surface of the first ring. The pair of buttons are configured to be depressed to become engaged with the first ring and compress the first ring toward the first holding component such that the second holding component is held in place only by means of the first spring, and to release the pressure between the second holding component and the replica tape from the first spring by applying a second predetermined force, which is greater than the first predetermined force, against the first spring to retract the first spring away from the first holding component.

According to an exemplary embodiment, the apparatus includes a second ring affixed to at least one point along a periphery of the second holding component between the first and second surfaces of the second holding component. The second spring is arranged above the second ring in the second direction.

According to an exemplary embodiment, the processing unit is configured to record in a memory unit the received measured light intensity at the at least two measurement points, and convert the measured light intensity at the at least two measurement points by substituting the recorded measured light intensity with thickness values recorded in a look-up table in association with corresponding values of the measured light intensity, respectively.

According to an exemplary embodiment, the apparatus includes an operator interface processing unit configured to receive an operator input to update the thickness values recorded in the look-up table.

According to an exemplary embodiment, the operator interface processing unit is configured to receive an update to the thickness values based on a linearization of a response function for the replica tape.

According to an exemplary embodiment, the apparatus includes a display unit configured to display at least one of: (i) a two-dimensional rendering of the thickness values corresponding to the measured light intensity at the at least two measurement points, and (ii) a two-dimensional rendering of a three-dimensional surface of the replica tape based on the thickness values corresponding to the measured light intensity at the at least two measurement points.

According to an exemplary embodiment, the processing unit is configured to generate an image in which a portion of the replica tape having the maximum thickness of the replica tape is correlated with a darkest area of the image to correct for variations between samples of the replica tape.

According to an exemplary embodiment, the look-up table is based on measured thickness values of the replica tape in association with corresponding measured light intensities that are stored after calibration with measured thickness values of an uncompressed, unembossed or uncast replica tape in association with corresponding measured light intensities of the uncompressed, unembossed or uncast replica tape.

According to an exemplary embodiment, the look-up table is based on measured thickness values recorded without being associated with measured light intensities of measurement points of the replica tape to account for at least one of (i) variations in measurements, (ii) changes to mechanical components of the apparatus, and (iii) buildup of debris in the apparatus.

According to an exemplary embodiment, the processing unit is configured to record in a memory unit the received measured light intensity at the at least two measurement points, and convert the measured light intensity at the at least two measurement points by applying an algorithm to the recorded measured light intensity to obtain corresponding thickness values for the measured light intensity at the at least two measurement points, respectively.

According to an exemplary embodiment, the apparatus includes an operator interface processing unit configured to receive an operator input to update the thickness values recorded in the look-up table.

According to an exemplary embodiment, the operator interface processing unit is configured to receive an update to the thickness values based on a linearization of a response function for the replica tape.

According to an exemplary embodiment, the apparatus includes a display unit configured to display at least one of: (i) a two-dimensional rendering of the thickness values corresponding to the measured light intensity at the at least two measurement points, and (ii) a two-dimensional rendering of a three-dimensional surface of the replica tape based on the thickness values corresponding to the measured light intensity at the at least two measurement points.

According to an exemplary embodiment, the processing unit is configured to generate an image in which a portion of the replica tape having the maximum thickness of the replica tape is correlated with a darkest area of the image to correct for variations between samples of the replica tape.

According to an exemplary embodiment, the algorithm is based on measured thickness values of the replica tape in association with corresponding measured light intensities that are recorded after calibration with measured thickness values of an uncompressed, unembossed or uncast replica tape in association with corresponding measured light intensities of the uncompressed, unembossed or uncast replica tape.

According to an exemplary embodiment, the algorithm is based on measured thickness values recorded without being associated with measured light intensities of measurement points of the replica tape to account for at least one of (i) variations in measurements, (ii) changes to mechanical components of the apparatus, and (iii) buildup of debris in the apparatus.

According to an exemplary embodiment, the processing unit is configured to determine at least one marking in the replica tape to distinguish between different grades of the replica tape, and adjust corresponding thickness values associated with the measured light intensities at the at least two measurement points based on a particular grade of the replica tape.

According to an exemplary embodiment, the first holding component includes a transparent window, and the second holding component includes a translucent anvil.

According to an exemplary embodiment, the first and second holding components are each respectively comprised of a support structure for supporting the replica tape therebetween and one of a window and a hole arranged in the corresponding support structure to enable light from the light source to be transmitted therethrough.

An exemplary embodiment of the present disclosure provides a method for characterizing a replica tape. The exemplary method includes embossing, compressing or casting the replica tape on a surface of a material to be measured, where the embossed, compressed or cast replica tape has a compressible surface which replicates the surface of the material. The exemplary method also includes securing the replica tape between a first holding component and a second holding component such that the compressible surface of the replica tape is secured against the first holding component. In addition, the exemplary method includes transmitting light through the second holding component, the replica tape and the first holding component, and measuring, in an image sensor, an intensity of the light respectively transmitted through at least two measurement points of the compressible surface of the replica tape. The exemplary method also includes converting, in a processing unit, the measured light intensity transmitted through the at least two measurement points into at least two data values each respectively relating to a measurement statistic of the replica tape at a corresponding one of the at least two measurement points, respectively. According to an exemplary embodiment, the method includes generating and displaying a two-dimensional representation of the converted data values. The generated and displayed two-dimensional representation of the converted data values includes at least one of: (i) a two-dimensional rendering of thickness values of the replica tape corresponding to the measured light intensity at the at least two measurement points, and (ii) a two-dimensional rendering of a three-dimensional surface of the replica tape based on the thickness values corresponding to the measured light intensity at the at least two measurement points.

According to an exemplary embodiment of the method, the generating and displaying of the two-dimensional representation of the converted data values includes generating an image in which a portion of the replica tape having the maximum thickness of the replica tape is correlated with a darkest area of the image to correct for variations between samples of the replica tape.

According to an exemplary embodiment of the method, a conductive element is attached to at least one point on a periphery of the second holding component between opposing surfaces of the second holding component. The second holding component and the conductive element attached to the second holding component are movable in a direction of the thickness of the replica tape. The exemplary method can also include measuring a height of the conductive element above the first holding component, measuring a height of the second holding component based on the measured height of the conductive element, and converting the measured height of the second holding component to a peak to valley thickness according to the measured height of the second holding component.

According to an exemplary embodiment of the method, the replica tape includes a transparent backing attached to the first surface of the replica tape. The second holding component is pressable against the transparent backing to secure the replica tape between the first and second holding components. A conductive element is attached to at least one point on a periphery of the second holding component between opposing surfaces of the second holding component. The second holding component and the conductive element attached to the second holding component are movable in a direction of the thickness of the replica tape. The exemplary method can include measuring a height of the conductive element above the first holding component, measuring a height of the second holding component based on the measured height of the conductive element, and converting the measured height of the second holding component to a peak to valley thickness by subtracting the measured height of the second holding component from a thickness of the transparent backing.

According to an exemplary embodiment of the method, the converting of the measured light intensity includes recording in a memory unit the received measured light intensity at the at least two measurement points, and converting the measured light intensity at the at least two measurement points by substituting the recorded measured light intensity with thickness values recorded in a look-up table in association with corresponding values of the measured light intensity, respectively.

According to an exemplary embodiment of the method, the look-up table is based on measured thickness values of the replica tape in association with corresponding measured light intensities that are stored after calibration with measured thickness values of an uncompressed, unembossed or uncast replica tape in association with corresponding measured light intensities of the uncompressed, unembossed or uncast replica tape.

According to an exemplary embodiment of the method, the converting of the measured light intensity includes recording in a memory unit the received measured light intensity at the at least two measurement points, and converting the measured light intensity at the at least two measurement points by applying an algorithm to the recorded measured light intensity to obtain corresponding thickness values for the measured light intensity at the at least two measurement points, respectively.

According to an exemplary embodiment of the method, the algorithm is based on measured thickness values of the replica tape in association with corresponding measured light intensities that are recorded after calibration with measured thickness values of an uncompressed, unembossed or uncast replica tape in association with corresponding measured light intensities of the uncompressed, unembossed or uncast replica tape.

An exemplary embodiment of the present disclosure provides an apparatus for characterizing a replica tape which has been embossed, compressed or cast on a surface of a material. The replica tape includes a first surface and an opposing second surface replicating the surface of the material on which the replica tape was embossed, compressed or cast. The second surface of the replica tape has a plurality of measurement points extending along a first direction substantially perpendicular to a thickness of the replica tape extending in a second direction between the first and second surfaces of the replica tape. The exemplary apparatus includes a mobile processing device including a camera and a processing unit. In addition, the exemplary apparatus includes a holding component having opposing first and second surfaces in the second direction. The first surface of the holding component is configured to be arranged proximate to the camera of the mobile processing device, and the second surface of the holding component is configured to secure the first surface of the replica tape to the holding component. The camera of the mobile processing device is configured to measure an intensity of light transmitted in the second direction through at least two of the plurality of measurement points of the second surface of the replica tape, respectively. The processing unit of the mobile processing device is configured to receive the measured intensity of the light transmitted through the at least two of the plurality measurement points and convert the measured light intensity at the at least two measurement points into at least two data values each respectively relating to a measurement statistic of the replica tape at a corresponding one of the at least two measurement points, respectively. According to exemplary embodiment of the apparatus, the light is transmitted to the second surface of the replica tape from at least one of an ambient light and an external light source.

According to an exemplary embodiment of the apparatus, the processing unit is configured to determine a peak to valley thickness of the at least two measurement points based on a measured thickness of the replica tape.

According to an exemplary embodiment of the apparatus, the processing unit is configured to record in a memory unit the received measured light intensity at the at least two measurement points, and convert the measured light intensity at the at least two measurement points by substituting the recorded measured light intensity with thickness values recorded in a look-up table in association with corresponding values of the measured light intensity, respectively.

According to an exemplary embodiment, the apparatus includes an input unit configured to receive an operator input to update the thickness values recorded in the look-up table.

According to an exemplary embodiment, the apparatus includes a display unit configured to display at least one of: (i) a two-dimensional rendering of the thickness values corresponding to the measured light intensity at the at least two measurement points, and (ii) a two-dimensional rendering of a three-dimensional surface of the replica tape based on the thickness values corresponding to the measured light intensity at the at least two measurement points.

According to an exemplary embodiment of the apparatus, the processing unit is configured to generate an image in which a portion of the replica tape having the maximum thickness of the replica tape is correlated with a darkest area of the image to correct for variations between samples of the replica tape.

According to an exemplary embodiment of the apparatus, the look-up table is based on measured thickness values of the replica tape in association with corresponding measured light intensities that are stored after calibration with measured thickness values of an uncompressed, unembossed or uncast replica tape in association with corresponding measured light intensities of the uncompressed, unembossed or uncast replica tape.

According to an exemplary embodiment of the apparatus, the look-up table is based on measured thickness values recorded without being associated with measured light intensities of measurement points of the replica tape to account for at least one of (i) variations in measurements, (ii) changes to mechanical components of the apparatus, and (iii) buildup of debris in the apparatus.

According to an exemplary embodiment of the apparatus, the processing unit is configured to record in a memory unit the received measured light intensity at the at least two measurement points, and convert the measured light intensity at the at least two measurement points by applying an algorithm to the recorded measured light intensity to obtain corresponding thickness values for the measured light intensity at the at least two measurement points, respectively.

According to an exemplary embodiment, the apparatus includes an input unit configured to receive an operator input to update the thickness values recorded in the look-up table.

According to an exemplary embodiment, the apparatus includes a display unit configured to display at least one of: (i) a two-dimensional rendering of the thickness values corresponding to the measured light intensity at the at least two measurement points, and (ii) a two-dimensional rendering of a three-dimensional surface of the replica tape based on the thickness values corresponding to the measured light intensity at the at least two measurement points.

According to an exemplary embodiment of the apparatus, the processing unit is configured to generate an image in which a portion of the replica tape having the maximum thickness of the replica tape is correlated with a darkest area of the image to correct for variations between samples of the replica tape.

According to an exemplary embodiment of the apparatus, the algorithm is based on measured thickness values of the replica tape in association with corresponding measured light intensities that are recorded after calibration with measured thickness values of an uncompressed, unembossed or uncast replica tape in association with corresponding measured light intensities of the uncompressed, unembossed or uncast replica tape.

According to an exemplary embodiment of the apparatus, the algorithm is based on measured thickness values recorded without being associated with measured light intensities of measurement points of the replica tape to account for at least one of (i) variations in measurements, (ii) changes to mechanical components of the apparatus, and (iii) buildup of debris in the apparatus.

According to an exemplary embodiment of the apparatus, the processing unit is configured to determine at least one marking in the replica tape to distinguish between different brands or grades of the replica tape, and adjust corresponding thickness values associated with the measured light intensities at the at least two measurement points based on a particular brand or grade of the replica tape.

According to an exemplary embodiment of the apparatus, the holding component includes a through-hole arranged between the first and second surfaces of the holding component to permit light transmitted through the replica tape to be received at the camera.

According to an exemplary embodiment of the apparatus, the holding component is translucent between the first and second surfaces of the holding component arranged between the camera and the replica tape.

According to an exemplary embodiment of the apparatus, the holding component includes a securing mechanism configured to secure the first surface of the replica tape to the second surface of the holding component.

An exemplary embodiment of the present disclosure provides a method for characterizing a replica tape. The exemplary method includes embossing, compressing or casting the replica tape on a surface of a material to be measured. The embossed, compressed or cast replica tape has a first surface and an opposing second surface which is compressible to replicate the surface of the material, where the second surface has a plurality of measurement points. The exemplary method also includes securing the replica tape to a holding component having a first surface and an opposing second surface such that the first surface of the replica tape is secured to the second surface of the holding component to expose the second surface of the replica tape to light. In addition, the exemplary method includes arranging the first surface of the holding component proximate to a camera of a mobile processing device. The exemplary method also includes measuring, in the camera of the mobile processing device, an intensity of light respectively transmitted through at least two of the measurement points of the second surface of the replica tape. Furthermore, the exemplary method includes converting, in a processing unit of the mobile processing device, the measured light intensity transmitted through the at least two measurement points into at least two data values each respectively relating to a measurement statistic of the replica tape at a corresponding one of the at least two measurement points, respectively.

According to an exemplary embodiment of the method, the light is transmitted to the second surface of the replica tape from at least one of an ambient light and an external light source.

According to an exemplary embodiment, the method includes measuring a thickness of the replica tape prior to the embossing, compressing or casting of the replica tape on the surface of a material.

According to an exemplary embodiment, the method includes determining, in the processing unit of the mobile processing device, a peak to valley thickness of the at least two measurement points based on the measured thickness of the replica tape.

According to an exemplary embodiment, the method includes generating and displaying a two-dimensional representation of the converted data values. The generated and displayed two-dimensional representation of the converted data values includes at least one of: (i) a two-dimensional rendering of thickness values of the replica tape corresponding to the measured light intensity at the at least two measurement points, and (ii) a two-dimensional rendering of a three-dimensional surface of the replica tape based on the thickness values corresponding to the measured light intensity at the at least two measurement points.

According to an exemplary embodiment of the method, the generating and displaying of the two-dimensional representation of the converted data values includes generating an image in which a portion of the replica tape having the maximum thickness of the replica tape is correlated with a darkest area of the image to correct for variations between samples of the replica tape.

According to an exemplary embodiment of the method, the converting of the measured light intensity includes recording in a memory unit the received measured light intensity at the at least two measurement points, and converting the measured light intensity at the at least two measurement points by substituting the recorded measured light intensity with thickness values recorded in a look-up table in association with corresponding values of the measured light intensity, respectively.

According to an exemplary embodiment of the method, the look-up table is based on measured thickness values of the replica tape in association with corresponding measured light intensities that are stored after calibration with measured thickness values of an uncompressed, unembossed or uncast replica tape in association with corresponding measured light intensities of the uncompressed, unembossed or uncast replica tape.

According to an exemplary embodiment of the method, the converting of the measured light intensity includes recording in a memory unit the received measured light intensity at the at least two measurement points, and converting the measured light intensity at the at least two measurement points by applying an algorithm to the recorded measured light intensity to obtain corresponding thickness values for the measured light intensity at the at least two measurement points, respectively.

According to an exemplary embodiment of the method, the algorithm is based on measured thickness values of the replica tape in association with corresponding measured light intensities that are recorded after calibration with measured thickness values of an uncompressed, unembossed or uncast replica tape in association with corresponding measured light intensities of the uncompressed, unembossed or uncast replica tape.

BRIEF DESCRIPTION OF THE DRAWINGS

Additional refinements, advantages and features of the present disclosure are described in more detail below with reference to exemplary embodiments illustrated in the drawings, in which:

FIG. 10 is a graphical representation illustrating intensity versus thickness as measured for a replica tape that has been embossed or compressed on the surface of a material to be measured, according to an exemplary embodiment of the present disclosure;

FIG. 11 is a graphical representation illustrating a modified intensity versus thickness characterization following scaling, according to an exemplary embodiment of the present disclosure;

Figure 1:
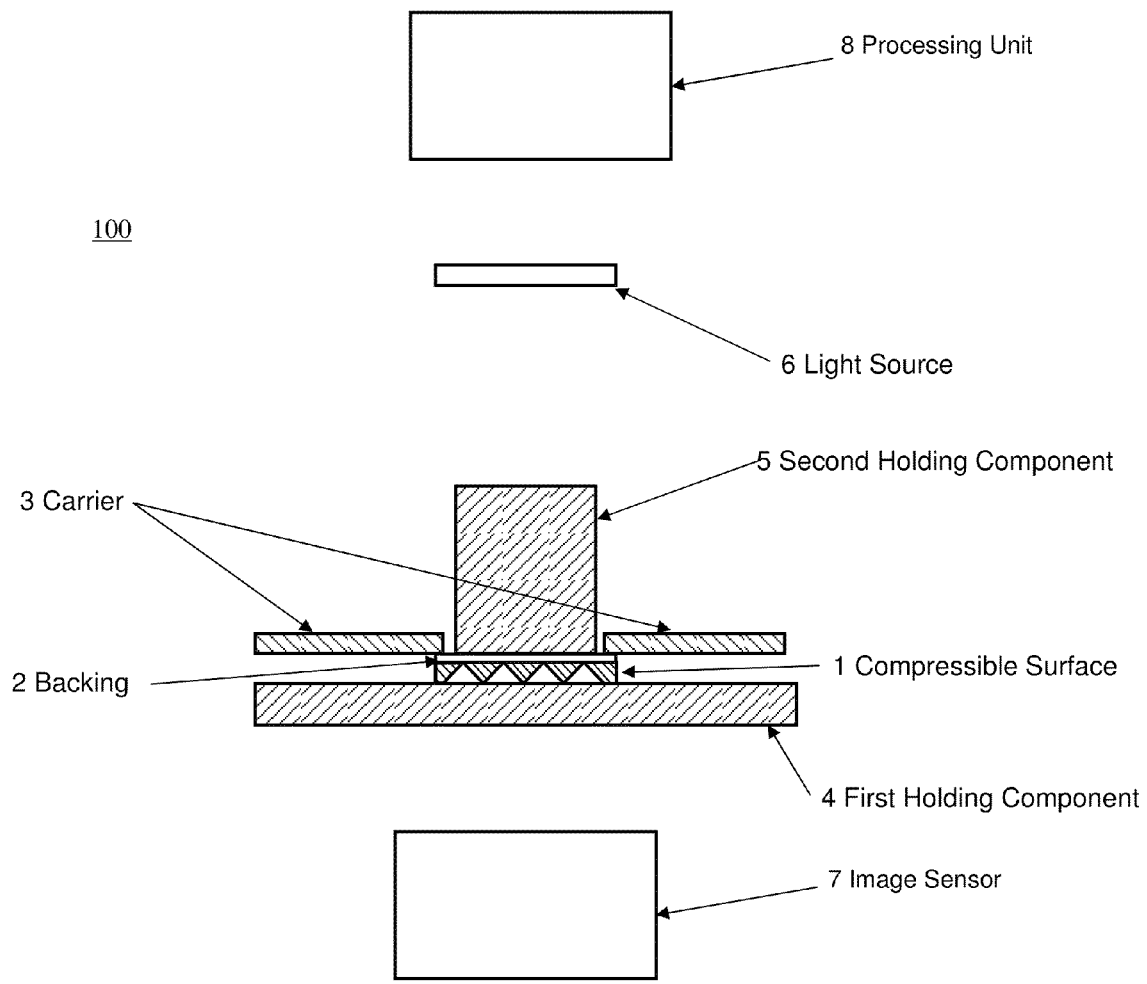
FIG. 1 is an exploded block drawing illustrating components of an apparatus for characterizing a replica tape according to an exemplary embodiment of the present disclosure.

In the drawings, identical or similarly functioning parts are denoted with the same reference symbols, unless otherwise noted. It is to be noted that components illustrated in the drawings are not shown to scale and may be shown in an exploded perspective to provide an explanatory description of such components.

DETAILED DESCRIPTION

Exemplary embodiments of the present disclosure solve the drawbacks noted above by providing a simple, low cost and portable apparatus for characterizing a replica tape replicating the surface of a material, as well as a method for characterizing a replica tape replicating the surface of a material. Exemplary embodiments of the present disclosure provide an apparatus and method which characterize a surface of a material on which a replica tape is embossed or compressed by transmitting light through the replica tape to determine characteristics of the surface in addition to the peak to valley distance measurement. According to an exemplary embodiment, the apparatus and method can also generate one or more images illustrating statistics of the characterized surface and/or a representation of the surface and display such images.

In the following description of exemplary embodiments of the present disclosure, a replica tape is embossed, compressed or cast to replicate a surface of a material in a manner described in the manufacturer's instructions. The replica tape is a mirror image of the original surface of the material on which the replica tape is embossed, compressed or cast. Hereinafter, the term "replica tape" means a medium or film that has been embossed, compressed or cast on a surface of a material in order to replicate that surface. Any medium or film that has a characteristic intensity versus thickness function can be utilized with the features of the present disclosure as described herein and is intended to be encompassed within the definition of a "replica tape" as used herein. For example, a cast methacrylate replica embedded with a pigment can be used. In the following description of exemplary embodiments, a replica tape is described as including a polyester backing 2 and a compressible foam 1 surface (see, e.g., FIG. 1). This is an example of a replica tape which may be utilized in the present disclosure, and the present disclosure is not limited thereto. For example, a replica tape may be composed of a backing that is made of a material other than polyester (e.g., nylon), and the compressible surface may be constituted by a material other than foam, where such material may be rigid. Alternatively, the replica tape may have only a compressible surface without any backing. For the sake of brevity, the term "replica tape" hereinafter refers to a replica tape which has been embossed, compressed or cast on a surface of a material to replicate that surface, unless otherwise noted.

FIG. 1 is an exploded block drawing illustrating components of an apparatus 100 for characterizing a replica tape according to an exemplary embodiment of the present disclosure. In accordance with an exemplary embodiment, a polyester backing 2 of replica tape is transparent, and a compressible surface (e.g., foam) 1 is translucent. In the example of FIG. 1, the polyester backing 2 of the replica tape is shown on one side of the replica tape, and the compressible surface 1 is shown on the other side of the replica tape. The compressible surface 1 of the replica tape has opposing first and second surfaces. In the example of FIG. 1, the first surface of the compressible surface 1 of the replica tape is attached to the polyester backing 2, while the second surface of the compressible surface 1 of the replica tape is the surface which is embossed, compressed or cast on the surface of a material to replicate that surface. The compressible surface 1 is illustrated in FIG. 1 as having been embossed, compressed or cast on a surface of a material to replicate the surface of that material. The polyester backing 2 of the replica tape may be attached to an adhesive paper carrier 3. When the replica tape is embossed, compressed or cast on the surface of a material, the compressible surface 1 of the replica tape has a plurality of measurement points extending along a first direction (e.g., horizontal direction in the example of FIG. 1) which is substantially perpendicular to a thickness of the replica tape extending in a second direction (e.g., vertical direction in the example of FIG. 1).

In accordance with an exemplary embodiment, the apparatus 100 includes a first holding component 4 having opposing first and second surfaces in the second direction. In the example of FIG. 1, the first surface of the first holding component 4 is the upper surface, and the second surface of the first holding component 4 is the lower surface. The first surface of the first holding component 4 is configured to support the compressible surface 1 of the replica tape thereon.

The exemplary apparatus 100 also includes a second holding component 5 having opposing first and second surfaces in the second direction. In the example of FIG. 1, the first surface of the second holding component 5 is the upper surface, and the second surface of the second holding component 5 is the lower surface. The second holding component 5 is configured to be pressed against the polyester backing 2 of the replica tape so as to secure the replica tape between the first surface of the first holding component 4 and the second surface of the second holding component 5. In accordance with an exemplary embodiment, the second holding component 5 is movable in the second direction to contact with the replica tape and hold the replica tape against the first holding component 4. The replica tape is thus held between the first and second holding components 4, 5 when the second holding component 5 is pressed against the polyester backing 2 of the replica tape.

It is conceived that the first and second holding components can be any type of structural component to achieve the function of securing the replica tape therebetween, as well as other operative functions as described herein. In accordance with an exemplary embodiment, the first holding component 4 can be a transparent window, and the second holding component 5 can be a translucent anvil. In accordance with this exemplary embodiment, the transparent window and translucent anvil may be fabricated from materials such as glass, quartz, polycarbonate, or other types of transparent and/or translucent material. The translucent anvil can function as a diffuser. As another example, the first and second holding components can each be support structures having a preconfigured window or hole arranged therein to permit light to be transmitted through the window or hole. For example, the first and second holding components can be configured as a rectangular, circular or semi-circular structures to secure the replica tape therebetween, while also permitting light to be transmitted through predetermined portions (e.g., central portions) of such structures. As another example, the first and second holding components can be opposing mirrors each having one reflective surface to reflect light and another surface to permit light to be transmitted therethrough. It is to be understood that the present disclosure is not limited to these exemplary structures of the first and second holding components 4, 5.

As noted above, the replica tape may not include a polyester backing. In this case, the second holding component 5 would be pressed against the first (uncompressed) surface of the replica tape to secure the replica tape between the first surface of the first holding component 4 and the second surface of the second holding component 5.

The exemplary apparatus 100 also includes a light source 6 arranged a first distance from the first surface of the second holding component 5. The light source 6 is configured to transmit light in the second direction through the first and second surfaces of the second holding component 5, the polyester backing 2 and compressible surface 1 of the replica tape, and the first and second surfaces of the first holding component 4. The light source 6 is configured to transmit light through a plurality of different measurement points on the compressible surface 1 of the replica tape simultaneously, such that a plurality of different measurement points on the compressible surface 1 are illuminated. The first distance of separation between the first surface of the second holding component 5 and the light source 6 is adjustable and may be dictated by the optics of the components used in the apparatus, such as the wavelength(s) of light emitted from the light source 6 and the desired area of the replica tape to be illuminated by the light source 6. In the exemplary embodiment illustrated in FIG. 1, the light source 6 is illustrated as transmitting the light through the polyester backing 2 and then through the compressible surface 1 of the replica tape, due to the arrangement of the light source 6 above the replica tape. However, it is also conceived that the light source 6 could be arranged below, for example, at a predetermined angle, below the replica tape such that the light is transmitted through the compressible surface 1 before being transmitted through the polyester backing 2 of the replica tape. In this configuration, the second surface of the second holding component 5 could be composed of a mirrored surface to reflect light transmitted through the polyester backing 2 back toward the compressible surface 1 of the replica tape.

In accordance with an exemplary embodiment, the light transmitted by the light source 6 may be within wavelengths of 200 to 1500 nm. That is, the light source 6 may transmit light from the ultraviolet (200 to 400 nm) to the visible (400 to 600 nm) and/or to the near infra-red (600 to 1500 nm) wavelengths. The exemplary apparatus 100 of FIG. 1 can be configured to use a light source 6 including a low-power infrared (IR) light emitting diode (LED) with a wavelength of 850 nm. Such an IR LED is commercially available and inexpensive. More than one wavelength of light may be transmitted, which may depend on the thickness or material characteristics of the replica tape.

The exemplary apparatus 100 also includes an image sensor 7 arranged a second distance from the second surface of the first holding component 4. The image sensor 7 is configured to measure an intensity of the light respectively transmitted through (i) the second holding component 5, (ii) at least two of the plurality measurement points on the compressible surface 1 of the replica tape, and (iii) the first holding component 4. In accordance with an exemplary embodiment, the image sensor 7 is configured to measure the intensity of the light transmitted through at least two of the plurality of measurement points by measuring the amplitude of a corresponding wavelength or range of wavelengths of the light transmitted through the measurement points, respectively. In accordance with an exemplary embodiment, the image sensor 7 can be a digital camera. It is to be understood, however, that the image sensor 7 can be any type of optical device which is able to measure an intensity of light in the range of wavelengths identified above. The second distance of separation between the second surface of the first holding component 4 and the image sensor 7 is adjustable and may be dictated by the optics of the components used in the apparatus, such as the wavelength(s) of light emitted from the light source 6, the desired area of the replica tape to be illuminated by the light source 6, and/or the desired focal point on the image sensor 7.

Figure 2:
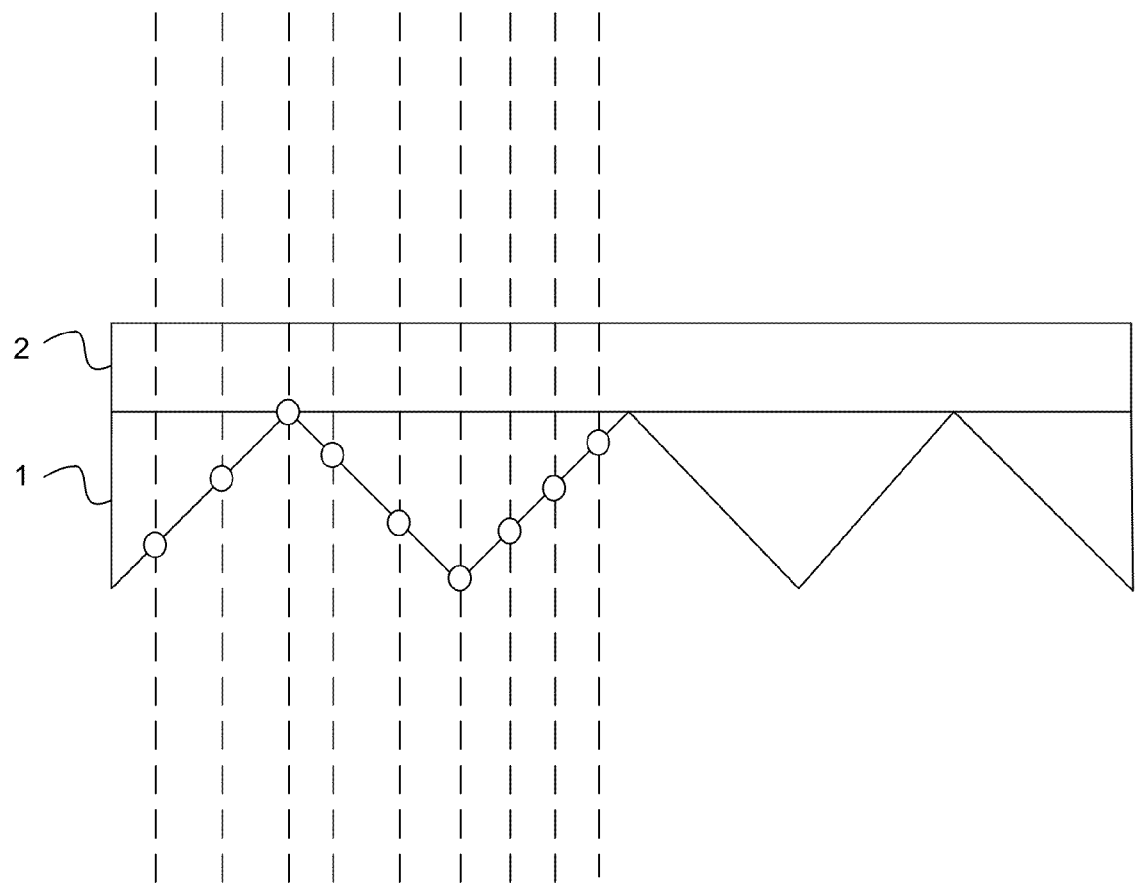
FIG. 2 is an explanatory diagram illustrating light transmitted through various measuring points of a replica tape, according to an exemplary embodiment of the present disclosure.

FIG. 2 is an exploded perspective view illustrating light being transmitted through a plurality of measurement points on the compressible surface 1 of the replica tape. For clarity of illustration, the first holding component 4, second holding component 5, light source 6 and image sensor 7 are omitted from FIG. 2. The dashed lines represent light being transmitted through the replica tape. The enlarged circles represent different measurement points on the compressible surface 1 of the replica tape through which the light is transmitted. The image sensor 7 arranged below the first holding component 4 on which the compressible surface 1 of the replica tape is positioned, is configured to measure an intensity of the light respectively transmitted through the plurality of measurement points on the compressible surface 1 of the replica tape. In the explanatory drawing of FIG. 2, nine measurement points are illustrated. The image sensor 7 would thus be configured to be measure a corresponding intensity of light transmitted through each corresponding one of the nine different measurement points.

The exemplary apparatus 100 also includes a processing unit 8 configured to receive the measured intensity of the light transmitted at one or more of the plurality of measurement points, record the received light intensity at the particular measurement points, and convert the measured light intensity at the one or more of the plurality of measurement points into a corresponding data value for that measurement point. The converted data for each corresponding measurement point relates to a measurement statistic of the replica tape at that measurement point, respectively. Accordingly, if two measurement points are of interest, the processing unit 8 could be configured to convert the measured light intensity at those two measurement points into at least two data values each respectively relating to a measurement statistic at a corresponding one of those two measurement points, respectively. The functions of the processing unit 8 for converting the measured light intensity into various types of measurement statistics will be described in further detail below.

In the example of FIG. 1, the processing unit 8 is displayed as being above the light source 6. The present disclosure is not restricted to this configuration. FIG. 1 is an exploded perspective view to illustrate the different components of the exemplary apparatus 100. The processing unit 8 can be arranged in any conceivable position in the finalized apparatus.

The light transmission through the replica tape is related to the thickness at any particular position of the replica tape. The exemplary apparatus 100 of FIG. 1 thus characterizes the surface of the material on which the replica tape is embossed, compressed or cast to provide statistics of the original surface. The exemplary apparatus 100 can also perform additional functions of generating and displaying an image representing the original surface of the material and/or statistics about the original surface of the material. Additionally, displacement measurements representing replica tape thickness can be used to represent peak to valley height and/or used to compensate optical representations of the surface to a known thickness versus intensity profile. These additional processing functions will be described in further detail below.

According to an exemplary embodiment, infrared light is used to take advantage of inexpensive color digital imaging equipment. A known digital camera passes all incoming light through a filter (e.g., a Bayer filter) before it reaches an array of light sensors of a Complementary Metal Oxide (CMOS) camera or a Charge Coupled Device (CCD). The filter allows light corresponding to either red, blue, or green wavelengths to alternatively pass through to different light sensors of the camera. If the arrangement of the red, blue, and green filter sections of the filter are known, they can be cross-referenced with the light intensity values for each sensor of the camera to reconstruct the color and intensity of the incoming light. Although the filter allows reproduction of a color image using a CMOS camera, at least three sensors can be utilized to measure the red, green, and blue components of each section of transmitted light, effectively reducing the resolution of the CMOS camera, for example, by at least one-third.

Since only the intensity of the light transmitted through the replica tape is important for the present disclosure, there is no need to filter the transmitted light into its component colors. Accordingly, the filter can be bypassed or dispensed with such that each sensor of the CMOS camera can be used to measure the incoming light intensity. This enables the use of lower-cost digital imaging equipment. Light corresponding to infrared wavelengths has been found to pass through the filter unaffected. Accordingly, an exemplary embodiment of the present disclosure utilizes such infrared wavelengths to characterize measurement points of a replica tape. To prevent external light sources outside the infrared wavelength range from passing through the filter and impacting the light sensors on the CMOS camera unpredictably, a band-pass filter 14 can be placed in front of the CMOS camera such that only infrared light can enter it, as illustrated in the exemplary embodiment of FIG. 3. The image sensor 7 thus can be utilized to read an optical transmission at a plurality of measurement positions of the replica tape, for example, in an X-Y array. The second distance of separation between the second surface of the first holding component 4 and the image sensor 7 may be affected by the provision of the band-pass filter 14, since the band-pass filter 14 operates to pass light transmitted therethrough to one or more focal points.

Figure 3:
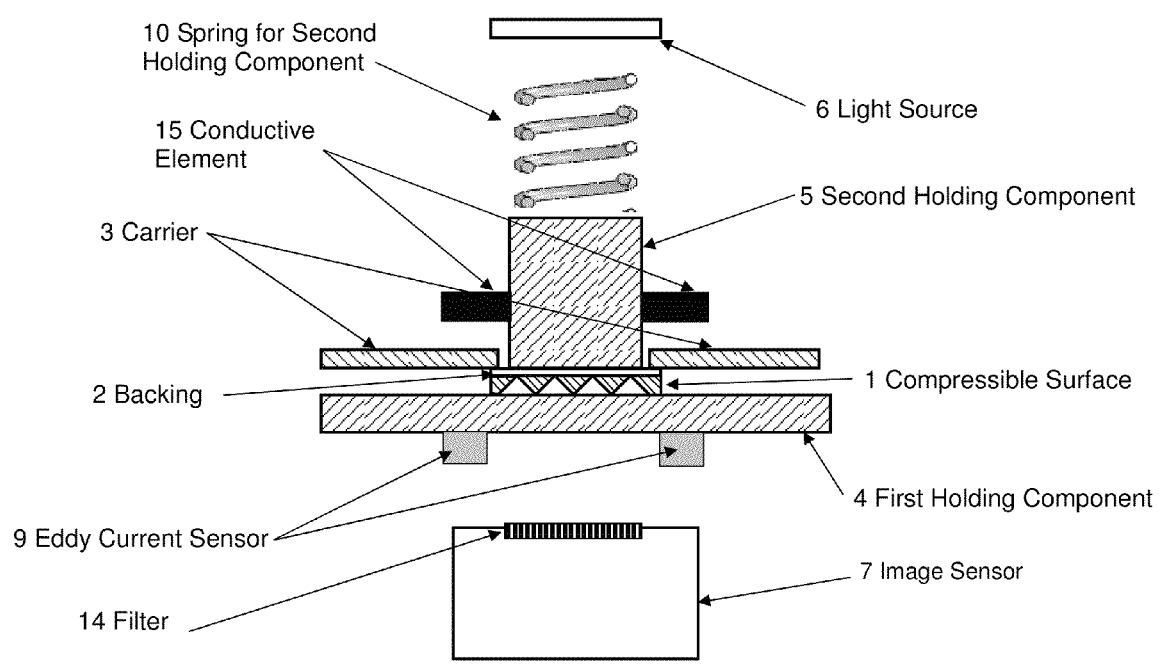
FIG. 3 is a block diagram illustrating components of an apparatus for characterizing a replica tape according to an exemplary embodiment of the present disclosure.

FIG. 3 illustrates an exemplary embodiment of the present disclosure for characterizing a surface of a material using a replica tape. The second holding component 5 is movable in the second direction (e.g., vertical direction in the example of FIG. 3) to contact with the replica tape and hold the replica tape flat against the first holding component 4. As noted above, the first and second holding components 4, 5 may be fabricated from glass, quartz, polycarbonate, or other material, for example. The exemplary apparatus also includes means to measure the height of the second holding component 5 above the first holding component 4. Such means can include, but not limited, for example, an eddy current sensor 9 placed beneath the first holding component 4 to measure the height of the second holding component 5 above the first holding component 4. The eddy current sensor 9 can be calibrated to measure the height of a conductive element 15 above the first holding component 4. In accordance with an exemplary embodiment, the conductive element 15 can be attached, either fixedly or removably, to at least one point on a periphery of the second holding component 5 between the first and second surfaces of the second holding component 5. The second holding component 5 and the conductive element 15 attached to the second holding component 5 are moveable in the second direction. The eddy current sensor 9 is configured to measure a height of the conductive element 15 above the first holding component 4. The processing unit 8 is configured to measure a height of the second holding component 5 based on the measured height of the conductive element 15, and convert the measured height of the second holding component 5 to a peak to valley thickness according to the measured height of the second holding component 5.

In the illustrated example of FIG. 3, a metal ring is illustrated as an example of the above-described conductive element 12 attached to at least one point on the periphery of the second holding component 5. In FIG. 3, the metal ring 15 is affixed to the second holding component 5 around a periphery of the second holding component 5 between the first and second ends of the second holding component 5. The ring 15 moves with the second holding component 5 since it is affixed thereto. If the replica tape does not include the polyester backing 2, the processing unit 8 can be configured to measure a height of the second holding component 5 based on a measured height of the metal ring 15, and convert the measured height of the second holding component 5 to a peak to valley thickness according to the measured height of the second holding component 5. In case the replica tape includes the polyester backing 2, the height of the second holding component 5 can be converted to a peak to valley thickness by the processing unit 8 subtracting the thickness of the polyester backing 2 of the replica tape from the measured height of the second holding component 5, which is based on the measured height of the ring 15. Accordingly, if the thickness of the polyester backing 2 of the replica tape is known or measured before the replica tape is embossed, compressed or cast on the surface of a material, the height of the second holding component 5 can be measured to ascertain a peak to valley thickness of the compressible surface 1 of the replica tape after it has been embossed, compressed or cast on the surface of a material.

In accordance with an exemplary embodiment, the second holding component 5 can itself can be at least partially composed of a conductive material such as a transparent conductive film, for example, Indium Tin Oxide or Zinc Oxide, in which case the conductive element attached to the second holding component 5 can be dispensed with. The eddy current sensor 9 can then measure a height of the second holding component 5 above the first holding component 4, and the processing unit 8 can in turn convert the measured height of the second holding component 5 to a peak to valley thickness according to the measured height of the second holding component 5.

The exemplary apparatus can also include other means to measure the height of the second holding component 5 above the first holding component 4. Such means can include, for example, the use of an eddy current, or magnetic or optical methods. It is to be understood that the present disclosure is not limited to a particular technique for obtaining the displacement measurement of the second holding component 5 above the first holding component 4, since such a displacement measurement is utilized for calibration of intensity measurements through the replica tape.

In accordance with an exemplary embodiment of the present disclosure illustrated in FIG. 3, the pressure between the second holding component 5 and the replica tape can be kept constant regardless of operator input, to prevent inadvertent compression of the compressible foam 1, by means of a spring 10 which applies a desired force onto the second holding component 5. The spring 10 may hereinafter be referred to as the spring 10 for the second holding component.

In accordance with an exemplary embodiment of the present disclosure, the eddy current sensor 9 is configured to determine when to characterize the replica tape. When the eddy current sensor 9 detects that the conductive element 15 (e.g., metal ring) is within a predetermined range, for example, less than or equal to the tape thickness, and is no longer moving, the processing unit 8 of the apparatus 100 characterizes the replica tape while the second holding component 5 is in the correct position, without any operator input.

Figure 4:
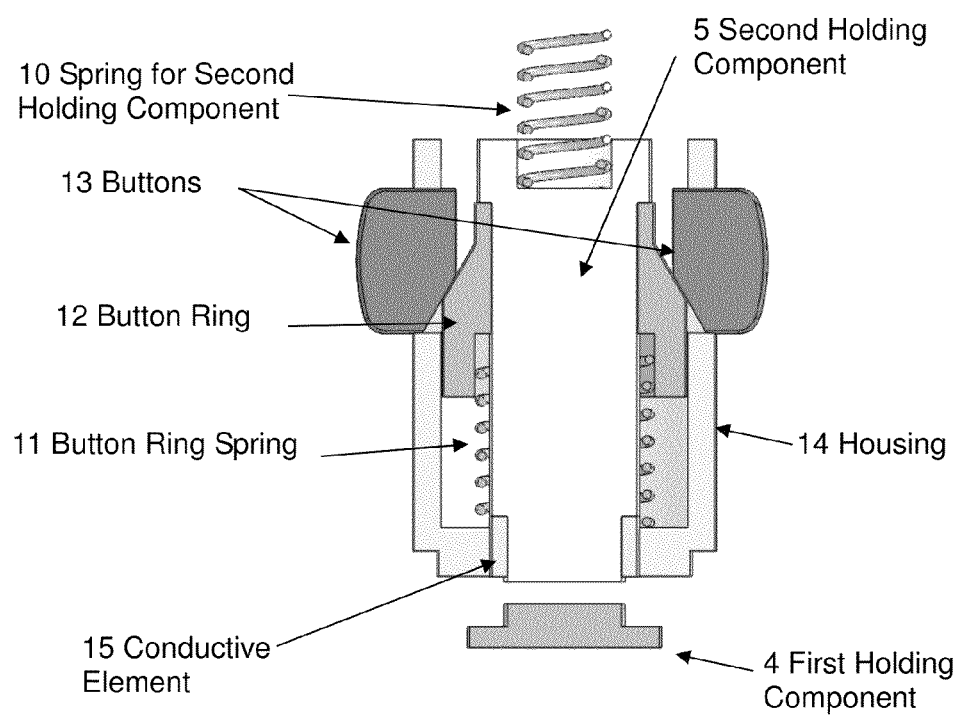
FIG. 4 is a block diagram illustrating components of an apparatus for characterizing a replica tape according to an exemplary embodiment of the present disclosure.

In accordance with an exemplary embodiment of the present disclosure illustrated in FIG. 4, the operator can, when desired, depress buttons 13 such that a button ring 12 is forced down against a button ring spring 11, towards the first holding component 4. The second holding component 5 is then held against the replica tape using only the force of the spring 10 for the second holding component. After characterization of the replica tape is complete, the operator can retract the second holding component 5 using the force of the button ring spring 11, which can be made greater than the force of the spring 10 for the second holding component, and remove the replica tape from the exemplary apparatus 100. Accordingly, as illustrated in FIG. 4, an exemplary embodiment of the present disclosure provides that the spring 10 is configured to apply a first predetermined force to the first surface of the second holding component 5 to keep pressure between the second holding component 5 and the replica tape constant, regardless of operator input. In the exemplary embodiment of FIG. 4, the ring 15, as an example of a conductive element, is fixed around a periphery of the second holding component between the first and second ends of the second holding component 5, and the button ring spring 11 surrounds the second holding component 5 and is arranged above the ring 15. This configuration is exemplary and the present disclosure is not limited thereto. For instance, as described above, the conductive element 15 can be dispensed with if the second holding component 5 is itself at least partially composed of a conductive material, or a conductive material can be attached to at least one point on the periphery of the second holding component 5 between the first and second surfaces of the second holding component 5. The button ring 12 surrounds the second holding component 5, and has (i) an inner groove configured to accommodate and engage the button ring spring 11 between the first and second ends of the second holding component 5 and (ii) an outer tapered surface. The buttons 13 are respectively disposed on opposite sides of a housing 14 which surrounds the second holding component 5. Each of the buttons 13 includes an inner tapered surface matching a contour of the outer tapered surface of the button ring 12. The buttons 13 are configured to be depressed to become engaged with the button ring spring 11 and compress the button ring spring 11 toward the first holding component 4 such that the second holding component 5 is held in place by means of the spring 10 for the second holding component, and to release the pressure between the second holding component 5 and the replica tape from the spring 10 for the second holding component by applying a second predetermined force, which is greater than the first predetermined force, against the spring 10 for the second holding component to retract the spring 10 away from the first holding component 4. Such a configuration advantageously permits an operator to use one hand to hold the exemplary apparatus 100, while using the other hand to guide the replica tape through the apparatus 100.

The processing functions of the exemplary apparatus for characterizing a replica tape will now be described with reference to FIG. 5, which is a block diagram illustrating components of the exemplary apparatus. The exemplary apparatus of FIG. 5 includes an image sensor 201, a light Source 202, and a thickness sensor 203 electrically connected to an image processor 205. The image sensor 201 corresponds to the image sensor 7 illustrated in FIGS. 1 and 3. The light source 202 corresponds to the light source 6 illustrated in FIGS. 1 and 3. The thickness sensor 203 corresponds to the features of the first holding component 4, second holding component 5, ring 8 and eddy current sensor 9 as described above with reference to FIG. 3. The replica tape 204 corresponds to the replica tape 1, 2 illustrated in FIGS. 1 and 3. The image processor 205 corresponds to the processing unit 8 illustrated in FIG. 1.

In accordance with the description of the aforementioned exemplary embodiments, the image processor 205 receives from the image sensor 201 the measured intensity of light transmitted through a plurality of measurement points on the replica tape. The image processor 205 is configured to store the received measured intensities and convert the measured intensities into data values each respectively relating to a measurement statistic of the replica tape at a corresponding one of the plurality of measurement points, respectively.

Image processor 205 responds to commands from operator interface 206 as a result of operator actions to direct the apparatus to perform a measurement. Display unit 207 is utilized to present the resulting measurements to the user, such as a digital rendition of the surface of the replica tape and/or statistics of particular measurement points. The results can be in the form of images and/or other metrics used to present surface profile characteristics.

Figure 5:
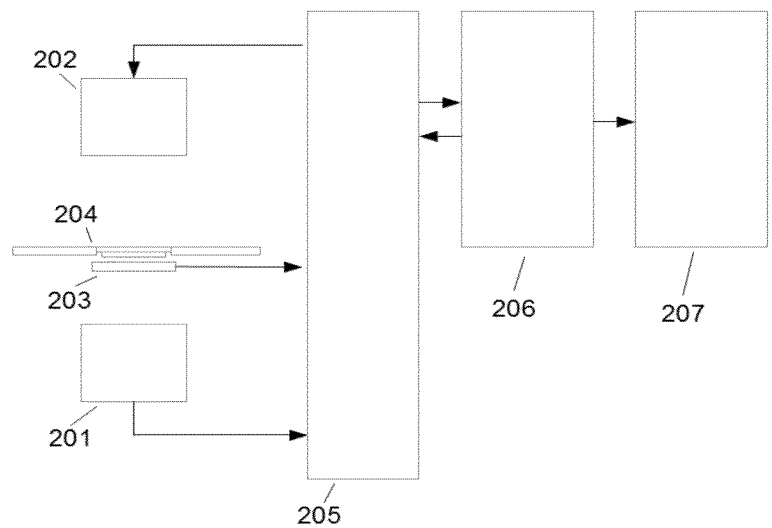
FIG. 5 is a block diagram illustrating components of an apparatus for characterizing a replica tape according to an exemplary embodiment of the present disclosure.
Figure 6:
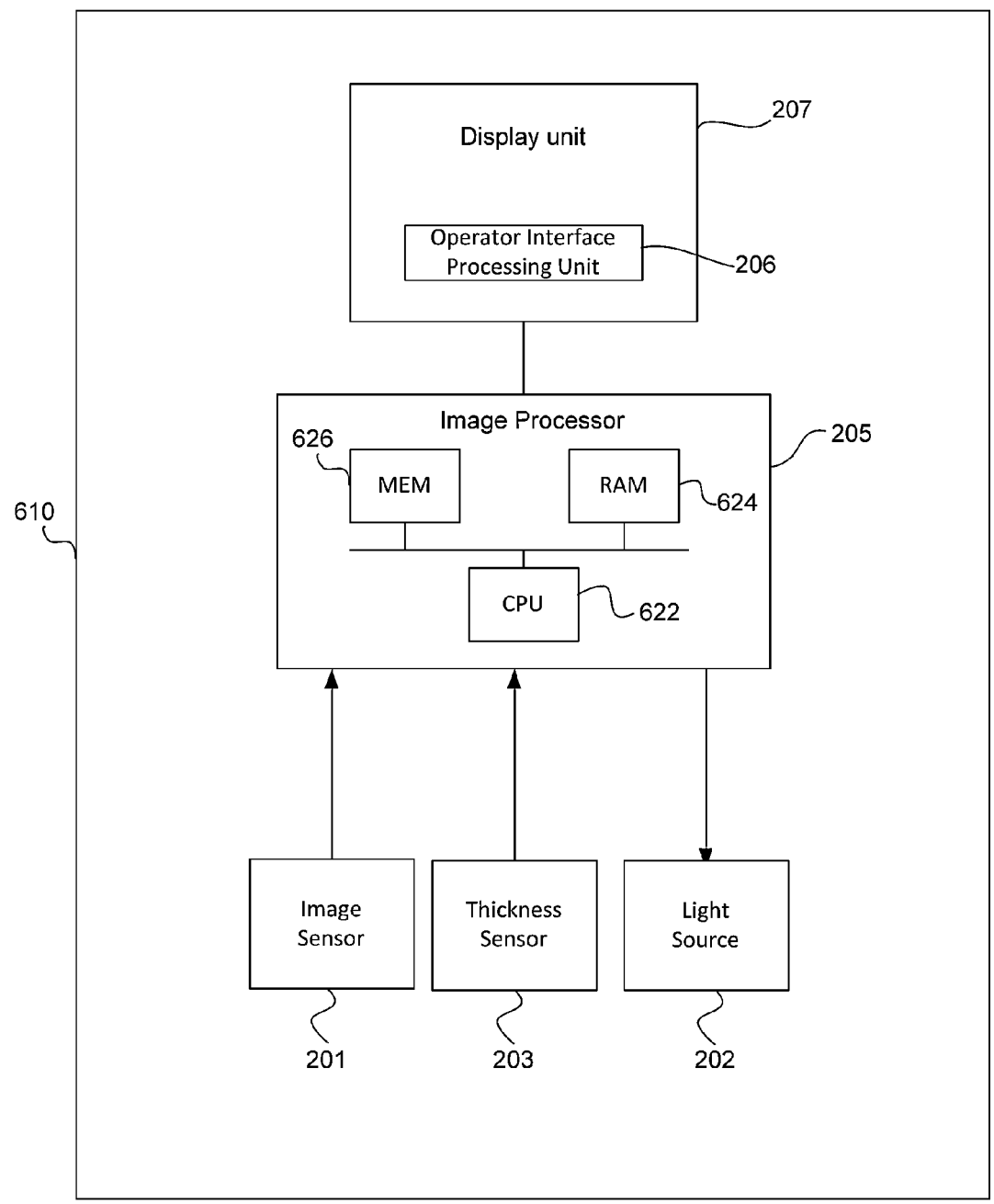
FIG. 6 is a block diagram illustrating components of an apparatus for characterizing a replica tape according to an exemplary embodiment of the present disclosure.

FIG. 6 illustrates a block diagram of components of the exemplary apparatus illustrated in FIG. 5 in more detail. In FIG. 6, the exemplary apparatus includes a housing 610 in which are provided the image sensor 201, light source 202, thickness sensor 203, image processor 205, operator interface processing unit 206, and display unit 207. The operator interface processing unit 206 is configured to display user-selectable operation instructions and any other information for the operation of the apparatus, while the display unit 207 is configured to display measurement results. In the example of FIG. 6, the operator interface processing unit 206 is illustrated as being comprised in the display unit 207. For example, the operator interface processing unit 206 could be a touchscreen display in which a user can enter input commands via the display unit 207. However, it is conceived that the operator interface processing unit 206 may be provided separate from the display unit 207 and include physical input means such as keys, trackpads, buttons, etc.

The image processor 205 includes a computer processor (e.g., a general-purpose processor such as an Intel® Core®, Pentium® or Celeron® processor or an AMD® Phenom®, Athlon® or Opteron® processor, an application specific processor such as an application-specific integrated circuit (ASIC), or a Digital Signal Control (DSC) processor) that is configured to control the operations of the apparatus. In the example of FIG. 6, the image processor 205 is illustrated as including a non-transitory, non-volatile memory (MEM) 626 on which a computer program and/or computer-readable instructions is/are tangibly recorded. The processor (CPU) 622 is configured to execute the program and/or instructions recorded on the memory 626 to carry out the operations and functions of the apparatus as described herein. The processor (CPU) 622 can also instruct the MEM 626 to record therein measurements of the intensity of light transmitted through a plurality of measurement points of the replica tape, as measured by the image sensor 201. In addition, the MEM 626 can have stored therein algorithms, look-up tables etc. for converting the measured light intensities into data values each respectively relating to a measurement statistic at a corresponding one of the measurement points for which the intensity of transmitted light was measured. The image processor 205 can also include a working memory such as a random access memory (RAM) 624 to utilize while performing its functions. The RAM 624 and MEM 626 can be provided separately from the processor 622, for example, in a different physical unit from the processor 622. The MEM 626 may be any type of non-volatile memory such as a read only memory (ROM), hard disk drive, flash memory, optical memory, etc.

Figure 7:
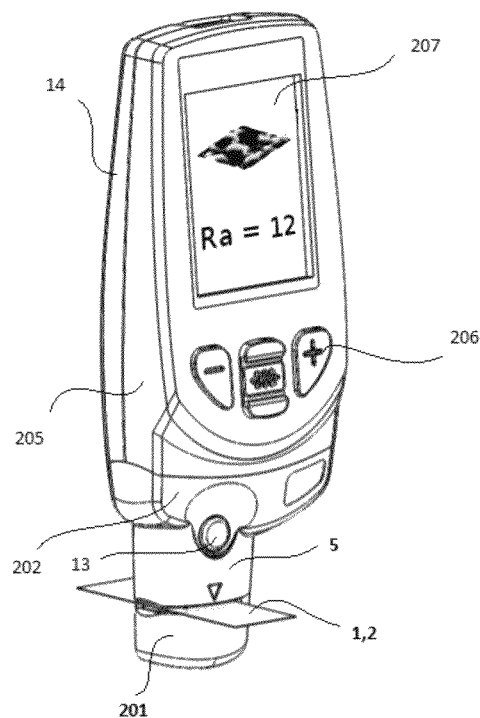
FIG. 7 is an illustration of an assembled apparatus according to an exemplary embodiment of the present disclosure.

FIG. 7 illustrates an example of an assembled apparatus including the above-described features of the present disclosure. The exemplary apparatus illustrated in FIG. 7 includes the image sensor 201 below the replica tape 1, 2, the second holding component 5 above the replica tape 1, 2, one or more of the depressible buttons 13 (the exemplary illustration of FIG. 7 includes one depressible button 13 on the front side of the apparatus, while another button 13 may be provided on the opposing back side of the apparatus), the light source 202 arranged above the second holding component 5, and the image processor 205, input unit operator interface processing unit 206 and display unit 207 arranged within the housing 14.

In accordance with the exemplary apparatus illustrated in FIGS. 5-7, it is possible to create a 3 dimensional (3-D) mapping of the intensity of the light transmitted from the light source 202 and passing through the replica tape 204 as measured by the image sensor 201 versus X and Y coordinates of the replica tape 204. The discrete intensity points of the intensity map can be translated to a thickness using a measure of the maximum thickness of replica tape 204 as measured using the thickness sensor 203 and applying a formula (e.g., algorithm) or look-up table to relate intensity to thickness. The resulting image represents a 3 dimensional thickness mapping of the replica tape 204. Since the embossed or compressed replica tape 204 is a representation of the surface profile of a test material, it is possible to relate the derived thickness mapping to the test surface and derive meaningful measures of the surface profile of the test surface using a simple, low cost hand held test instrument. 3D, 2D or 1D surface measures can be derived easily from the 3D map. Examples of measures that could be derived include:

(i) Ra: Arithmetic mean surface roughness along a line through an area, (ii) Rz: Surface roughness depth along a line through an area, (iii) Sa: Surface area roughness, (iv) Sdr: Developed surface area.

The following describes an example of converting the measured intensity of light transmitted through measurement points to thickness.

The following description of the features of the exemplary apparatus uses a characterization process to establish a base intensity to thickness function that is scaled using a maximum thickness of the embossed or compressed replica tape 204 during the image acquisition process. This function is applied to each x,y point of the replica tape 204 to create a thickness mapping for each intensity value measured at each x,y point of the acquired image that compensates for irregular illumination of the tape and accounts for variations in tape composition.

Figure 8:
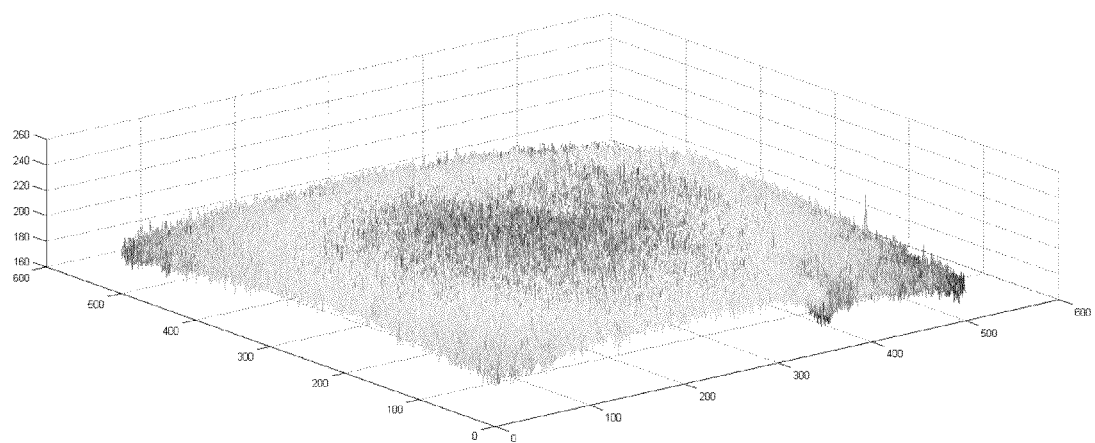
FIG. 8 is a graphical representation illustrating the intensity of light measured by an image sensor when no replica tape is present in the apparatus, according to an exemplary embodiment of the present disclosure.
Figure 9:
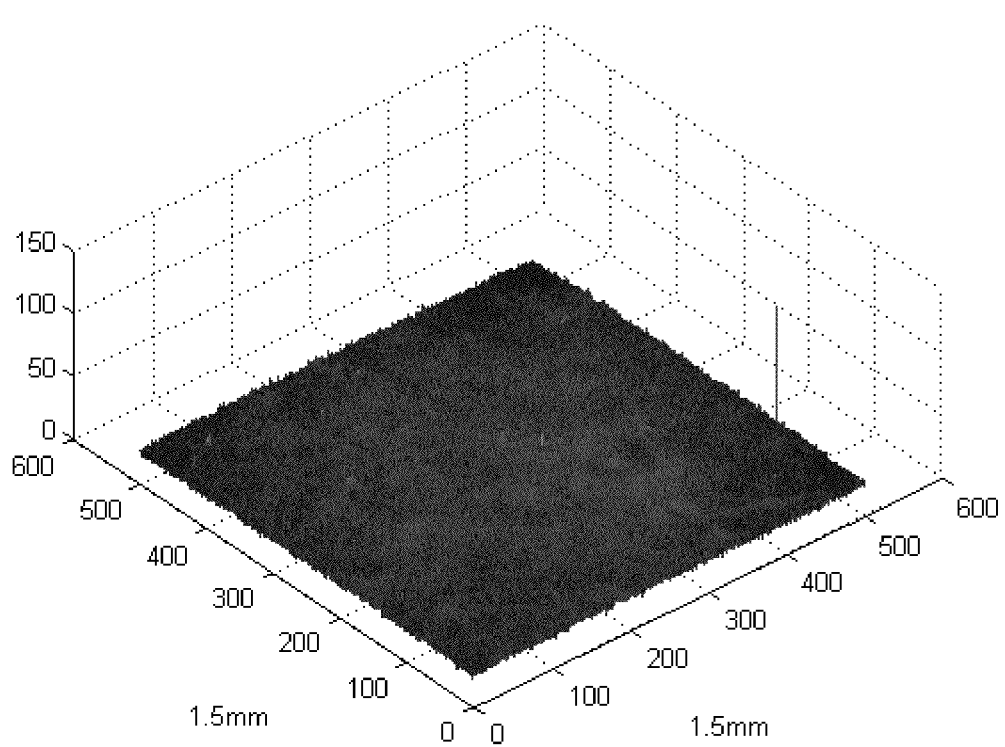
FIG. 9 is a graphical representation illustrating the intensity of light transmitted through a replica tape that is not embossed or compressed, according to an exemplary embodiment of the present disclosure.

To compensate for irregular illumination from the light source 202 and/or sensitivity changes of the image sensor 201, a characterization procedure is used to establish maximum and minimum light intensity where an intensity map is measured by the image sensor 201 and stored in the MEM 626 of the processor 205 for both an image with no tape present and an image of uncompressed replica tape 204. FIGS. 8 and 9 illustrate two such mappings.

FIG. 8 represents the intensity of light transmitted from the light sensor 202 as measured by the image sensor 201 when no replica tape is present in the apparatus. FIG. 9 represents the intensity of light passing through an uncompressed tape. During a measurement, each intensity measure at point x,y can now be normalized against the corresponding maximum light at x,y as measured when no replica is present and a minimum light at x,y when uncompressed replica tape is used. A measured image can now be constructed that ranges from 0 to 1 for each x,y point measured. The resulting image is compensated for uneven light distribution across the image plane and inconsistencies in the light intensity and tape composition. Since the characterization process can be performed by the operator or other end user, the apparatus can be constructed of less expensive optical components that may experience characteristic drift over time.

To translate intensity to thickness, a function defining characteristic normalized intensity has been empirically derived and stored in image processor 205 as function f1 and illustrated in FIG. 10.

When burnished on a rough material, replica tape 204 will be fully compressed at the peaks. This corresponds to the maximum intensity x,y of the image. The burnished replica tape 204 will be least compressed in the valleys. This corresponds to the minimum intensity. The thickness sensor 203 measures the maximum thickness of the replica tape 204 corresponding to the deepest valley or minimum intensity. To compensate for changes in composition of the replica tape 204, intensity variations of light sensor 202 and bulk image sensor 201 sensitivity drift, function f1 as illustrated in FIG. 10 can be shifted as illustrated in FIG. 11 where the new function f2 is a shifted version of f1 based on the measured maximum thickness using the thickness sensor 203 of the replica tape 204 that represents the darkest or least intensity x, y value in the image. Thus, for an acquired image, every x, y point of the measured image is analyzed to determine which x,y point has the lowest intensity. This corresponds to the maximum thickness and as such a scaling factor is derived by using the output of thickness sensor 203 to shift the y intercept of f1 to this thickness value. A new function f2 is thus created that relates thickness to normalized intensity of the measured image.

Accordingly, the present disclosure provides a mechanism to derive a thickness profile of a replica tape by using an independent measurement means to calibrate a characteristic intensity profile. The apparatus of the present disclosure can therefore be specifically constructed to derive a calibrated thickness profile of a replication media and specifically the replica tape. These means overcome the drawbacks associated with known techniques such as U.S. 2003/0222215, which provide for determining an intensity profile but do not provide means to perform in situ adjustments of the profile based on corresponding thickness measurements.

In addition to the technique described above with respect to FIGS. 10 and 11 for adjusting the thickness-intensity curve based on a measured thickness of the replica tape (e.g, by the use of an eddy current sensor), the present disclosure also provides another, optional technique for deriving an accurate measurement. This technique involves a linearization function to account for a replica tape's non-linear replication response to roughness. Replica tapes can have a different grade, or thickness, to cover a different range of profile heights of the surface to be replicated. For example, a first grade of replica tape may cover a range of profile heights approximately between 38 µm to 115 µm (1.5 to 4 mils). A second grade for lower profile heights can be used to extend the aforementioned range downward to 20 µm, so as to have a range of profile heights approximately between 20 µm to 63 µm (0.8 to 2.5 mils). The foregoing grades are examples of commercially available replica tape. The present disclosure is not limited to these examples.

Each grade of replica tape responds non-linearly at the lower end of its range—where the compressible surface becomes fully compressed—and at the upper end of its range—where the peak heights are greater than the thickness of the compressible surface. As the replica tape's response becomes increasingly non-linear, measurements become more inaccurate.

Replica tape thickness can be compared to a number of alternate methods to measure the height profile. Examples of such alternate techniques can include a drag stylus, needle type surface profile gages, or microscopy techniques such as interferometric or confocal. For example, the use of a thickness gage incorporating a digital processor (e.g., a processor as described above) allows for the display of linearized peak-to-valley profiles if the response function of the replica tape, relating replica thickness to height of the profile, is known. Suitable response curves can be deduced from experiments in which replica tape determinations of profile are plotted against profiles obtained with electronic stylus roughness instruments for different test surfaces. In general, stylus measurements display greater statistical noise than replica tape, but have the advantage of better linearity. Linearizing a replica tape's response combines the low statistical noise of replica tape with the linear behavior of a stylus.

Figure 12:
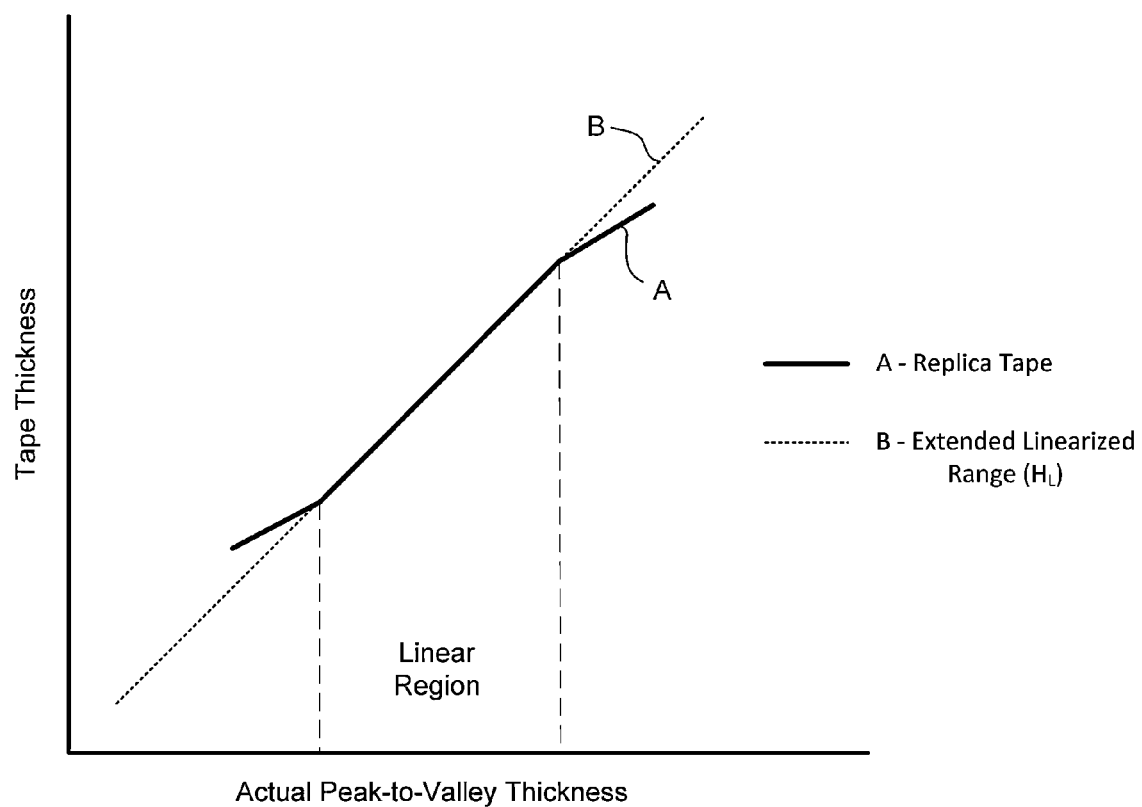
FIG. 12 is a graphical representation illustrating an observed response function of a replica tape in comparison to an extended linearization range, according to an exemplary embodiment of the present disclosure.

FIG. 12 illustrates the response function for a grade of replica tape, such as one of the aforementioned first or second grades of replica tape. The solid black line A shows, at the high end of the range of the replica tape, how the replica tape reads low where the peaks are higher than the thickness of the compressible surface of the replica tape. The solid black line A also shows, at the low end of the range of the replica tape, how the replica tape reads high as it nears full compression. In between, the replica tap exhibits a relatively linear response. Ideally, replica tape would follow line B representing an extended linearization range. The following linearization technique can be utilized to map the actual response of the replica tape onto line B.

First, a response function $f_{RT}$ of the replica tape as described above, relating the thickness of the replica tape $H_o$ (observed thickness) to digital stylus roughness, $R_t$, is derived for the replica tape as follows.

$$R_t = f_{RT}(H_o)$$

Provided the measuring instrument's processor is has been set to the appropriate grade, a processor's application of $f_{RT}$ to a replica thickness will have the effect of compensating for that grade of replica tape's compressible surface non-linearity. It does so, however, by converting $H_o$ to an $R_t$-equivalent value, which is only approximately equal to a replica profile.

Next, the $R_t$ value is mapped to a least squares straight line fit to the replica tape response curve, and it is the resulting linearized value of replica tape profile, $H_{lin}$, that is reported by the measuring instrument. This linearization technique can be applied for different grades of replica tape. In addition, the least squares straight line can be fit to the combined response curve of multiple grades of replica tape. With linearization, the process of obtaining a measurement is simplified, its reliability is increased, the possibility of operator error is reduced, and data recording and analysis are made more convenient.

In accordance with the aforementioned techniques for measuring the intensity of light transmitted through a plurality of measurement points of the replica tape 204 based on initial calibrations in accordance with thickness measurements of an uncompressed replica tape, the image processor 205 is thereby configured to convert the measured and recorded intensity of light transmitted through the plurality of measurement points into corresponding data values each representing a measurement statistic of the replica tape 204 at the corresponding measurement points of the replica tape 204. The image processor 205 of the exemplary apparatus is therefore able to provide a characterization of the recorded transmitted light intensity. Such characterization of the recorded light intensity can include, for example, but not limited to, converting the transmitted light intensity at one or more of a plurality of measurement points of the replica tape to an image representing the characterized surface of the material and/or other surface profile characteristics.

According to an exemplary embodiment, the characterization of the recorded transmitted light intensity can include, for example, but not limited to, converting the transmitted light intensity to a thickness of the replica tape at the position of the replica tape through which the transmitted light was transmitted. According to an exemplary embodiment, an algorithm or look-up table can be utilized for converting the transmitted light intensity to a thickness of the replica tape. In accordance with an exemplary embodiment, the algorithm or look-up table used to characterize the recorded transmitted light intensity can be created using experimentally derived data points, or a theoretical formula. Although the proportion of transmitted light intensity to replica tape thickness may remain constant over time and between apparatuses, mechanical variations and wear in the components may affect the intensity of transmitted light to the digital camera for all replica tape thicknesses.

Variations and wear in the components of the apparatus may cause differences in the recorded transmitted light intensity between apparatuses and over time. For example, it may be necessary to correct for uneven illumination and for variations in the photocells of the camera, or for a buildup of debris on the apparatus. An exemplary embodiment of the present disclosure also provides the functionality to facilitate an operator of the apparatus to make a 'zero' characterization in the absence of replica tape, and/or to modify the formula or look-up table used to characterize the recorded transmitted light intensity to correct for these factors. The correction may also include substituting the measurement from a gradient or formula from surrounding pixels in place of a defective pixel.

Manufacturing variations in the replica tape may also cause undesirable differences in the recorded transmitted light intensity between samples. An exemplary embodiment of the present disclosure provides the functionality to facilitate the operator to make a 'maximum' characterization using the known thickness of the unembossed, uncompressed or uncast replica tape, as described above. In accordance with an exemplary embodiment of the present disclosure, the thickness of the embossed tape can be measured using, for example, but not limited to, the eddy current principle or other common methods such as magnetic techniques. By correlating this known maximum thickness with the areas of the lowest transmitted light intensity to the digital camera, the look-up table or formula can be modified to correct for variations between each replica tape specimen.

Characterizing the replica tape thickness includes calculating statistics, for example, but not limited to, peaks per unit area, or peak area, or displaying a thickness along a line through operator-selected positions. Characterizing the replica tape may also include displaying a two dimensional representation of a three dimensional surface. The characterizing of the replica tape can also include displaying a false color representation wherein the color correlates to the thickness.

Various thicknesses of replica tape are available to measure different surface profile heights. In accordance with an exemplary embodiment of the present disclosure, the operator can account for the thickness of the replica tape by preforming a 'maximum' characterization when switching between different thicknesses of unembossed replica tape. In accordance with another exemplary embodiment, different thicknesses of replica tape can be identified using the digital camera within the present disclosure to read a marking present on the replica tape. This marking can include, but is not limited to, a colored area, barcode, QR code, pattern of lines, or a symbol. Depending on the marking identified by the digital camera, a different look-up table or formula may then be used to characterize the replica tape thickness.

The elements of the apparatus are simple, robust, low cost and can be made compact and portable. A portable apparatus is useful to qualify abrasive blasted surfaces in the field with a minimum of time delay.

Figure 13:
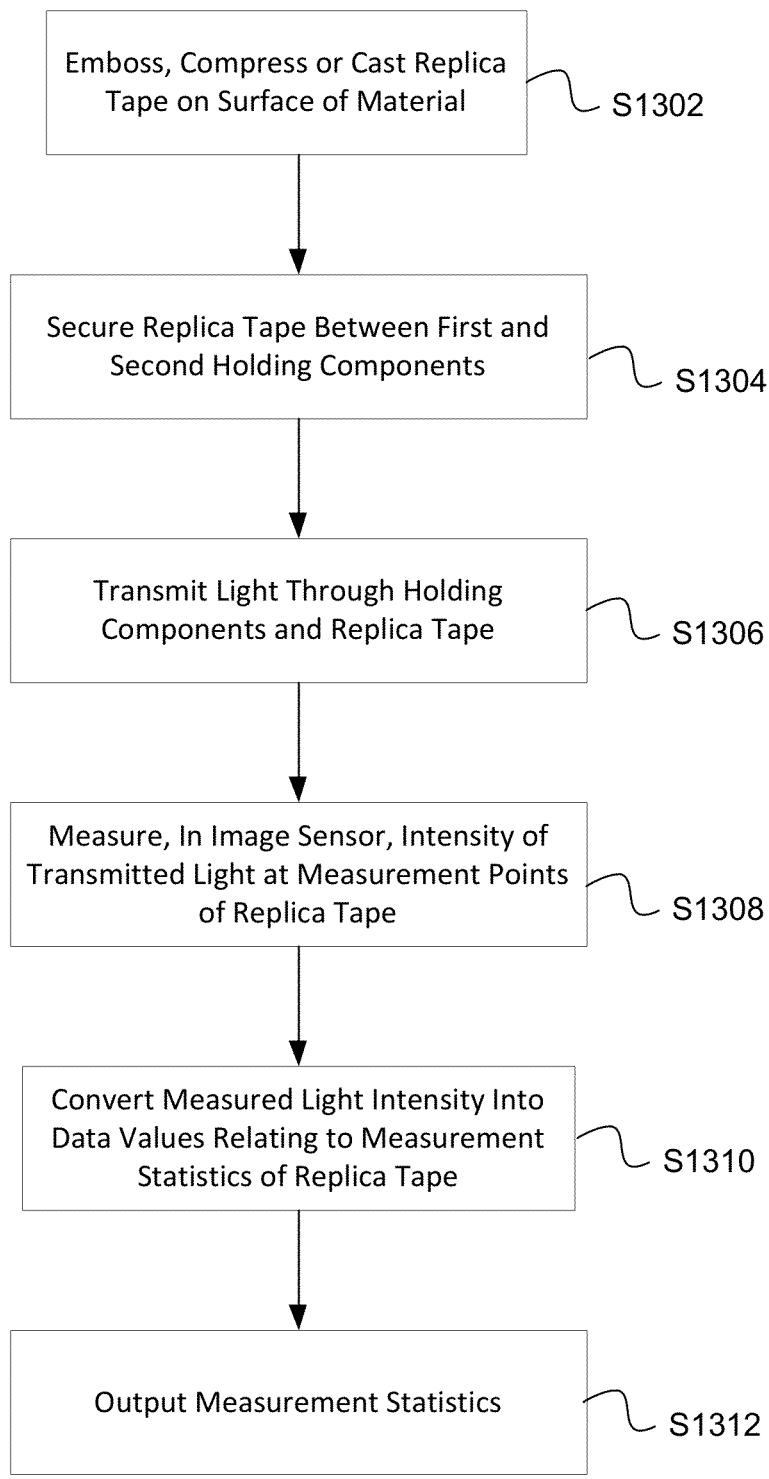
FIG. 13 is a flowchart illustrating steps of a method for characterizing a replica tape according to an exemplary embodiment of the present disclosure.

In accordance with the embodiments mentioned above, an exemplary embodiment of the present disclosure also provides a method for characterizing a surface of a material using a replica tape. FIG. 13 is a flowchart illustrating steps of an exemplary embodiment of the method according to the present disclosure. The exemplary method of the present disclosure includes embossing or compressing a replica tape on a surface of a material to be measured (S1302). The exemplary method also includes securing the replica tape between the first holding component (e.g., transparent window) and a second holding component (e.g., translucent anvil) such that the compressible foam surface of the replica tape is secured against the second holding component (S1304). In addition, the exemplary method includes transmitting light through the second holding component, the replica tape and the first holding component (S1306). As noted above, the transmitted light may have a wavelength of 200 to 1500 nm. The exemplary method also includes measuring, in an image sensor, an intensity of the light respectively transmitted through at least two measurement points of the compressible surface of the replica tape (S1308). The measurement of the intensity of the light transmitted through the at least two measurement points may include measuring a respective wavelength of the light transmitted through the at least two measurement points. Furthermore, the exemplary method includes converting the measured light intensity transmitted through the at least two measurement points into at least two data values each respectively relating to a measurement statistic of the replica tape at a corresponding one of the at least two measurement points, respectively (S1310). The exemplary method may also include generating and displaying a two-dimensional representation of the converted data values (S1312). The displayed representation may include, for example, an illustration of the characterized surface of the replica tape and/or an illustration of the surface of the replica tape. The exemplary method of the present disclosure may include any process steps in accordance with the operative features of the above-described apparatus.

In addition, an exemplary embodiment of the present disclosure provides a non-transitory computer-readable recording medium (e.g., MEM 626) having a computer program recorded thereon that causes the processor 622 of the image processor 205 to carry out operations corresponding to the above-described exemplary method.

Figure 14:
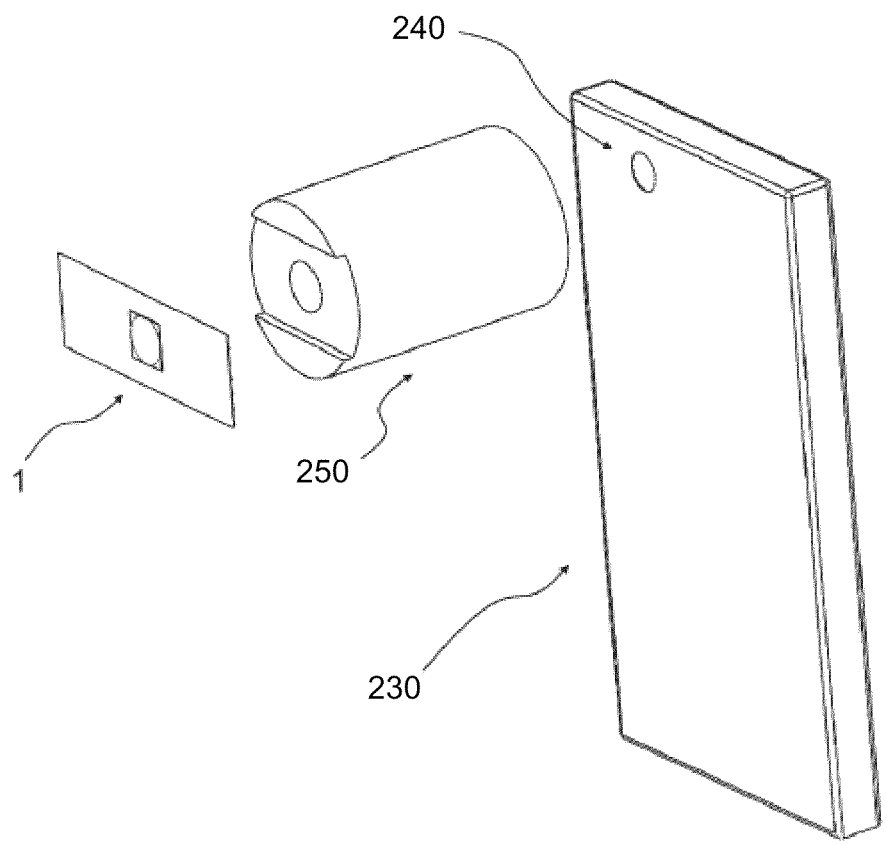
FIG. 14 is an exploded block drawing illustrating components of an apparatus for characterizing a replica tape according to an exemplary embodiment of the present disclosure.

In the above-described exemplary embodiments, the replica tape was described as being secured between the first and second holding components 4, 5. FIG. 14 illustrates an exploded perspective view of an apparatus 200 according to an exemplary embodiment of the present disclosure which includes a mobile processing device 230 having a camera 240 and a holding component 250 for characterizing a replica tape 1. In comparison to the apparatus 100 illustrated in FIG. 1, for example, which includes two holding components 4, 5 respectively arranged on opposite sides of the replica tape 1, the apparatus 200 illustrated in FIG. 14 includes a single holding component 250. In addition, the apparatus 200 illustrated in FIG. 14 differs from the apparatus 100 illustrated in FIG. 1 in that the image sensor 7 and processing unit 8 of the apparatus 100 are included in the mobile processing device 230 equipped with the camera 240. The mobile processing device 230 may be a smartphone (e.g., smartphones manufactured by Apple®, Samsung®, Motorola®, HTC®, Nokia®, etc.) and/or a portable computer such as a tablet computer (e.g., iPad®, Nexus®, Kindle®, etc.) or laptop computer, for example. It is also conceived that the mobile processing device 230 may be a desktop computer having a movable camera attached thereto.

In the above-described exemplary embodiments, the replica tape 1 was described as having a first surface and an opposing second surface replicating the surface of the material on which the replica tape 1 was embossed, compressed or cast, where the second surface of the replica tape 1 has a plurality of measurement points (see, e.g., FIG. 2) extending along a first direction substantially perpendicular to a thickness of the replica tape 1 extending in a second direction between the first and second surfaces of the replica tape 1. In the exemplary embodiment of FIG. 14, the holding component 250 is arranged between the first surface of the replica tape 1 and the side of the mobile processing device 230 on which the camera 240 is arranged. In the example of FIG. 14, the camera 240 is arranged on the back side of the mobile processing device 230, while the display and operator interface are arranged on the front side of the mobile processing device 230. According to an exemplary embodiment illustrated in FIG. 14, the holding component 250 has a first surface facing toward the camera 240 of the mobile processing device 230, and a second surface facing toward the replica tape 1. As illustrated in the example of FIG. 14, the second surface of the holding component 250 may have a groove formed therein to accommodate the width and length of the replica tape so that the burnished surface of the replica tape 1 can be arranged at an annular through-hole of the holding component 205. Alternatively, the second surface of the holding component 250 may be flat and have securing mechanisms such as clips to hold the replica tape 1 in place for characterizing the replica tape 1. It is also conceived that other securing mechanisms can be used to hold the burnished surface of the replica tape 1 at the through-hole of the holding component 250. For example, in case the replica tape has the backing 2 as described above, the backing 2 may have an adhesive surface for temporarily affixing the backing 2 to the second surface of the holding component 250. According to another example, the first surface of the replica tape 1 may be secured to the second surface of the holding component 250 by adhesive tape or be held to the second surface of the holding component 250 by a user. The foregoing are intended to be examples of securing the replica tape 1 to the second surface of the holding component 250, and the present disclosure is not limited thereto. In accordance with the exemplary embodiment of FIG. 14, a description of the replica tape 1 being secured to the holding component 250 is intended to include any means or mechanism for temporarily securing the replica tape 1 to the second surface of the holding component 1 so that the replica tape 1 can be characterized by the apparatus 200.

In the example of FIG. 14, the holding component 250 is illustrated as having a through-hole. The present disclosure is not limited to this example. For instance, the holding component 250 can be constituted of a translucent material without such a through-hole. The through-hole and/or translucent material are intended to enable light to reach the camera 204 of the mobile processing device 204 from the second surface of the replica tape 1 and measure an intensity of the light respectively transmitted through at least two of a plurality of measurement points of the second surface of the replica tape 1. In accordance with an exemplary embodiment, the light transmitted through the replica tape 1 and holding component 250 to reach the camera 204 can be ambient light of the location in which the exemplary apparatus 200 is utilized. Alternatively or in addition, the light transmitted through the replica tape 1 and holding component 250 to reach the camera 204 can be from a generally available or calibrated external light source such as a lamp, flashlight, etc. In the case of a calibrated external light source, the light source can be calibrated to transmit light within a configured wavelength range. For example, the calibrated external light source can be configured to transmit light within wavelengths of 200 to 1500 nm, as discussed above with respect to the light source 6 of the exemplary apparatus 100.

Figure 15:
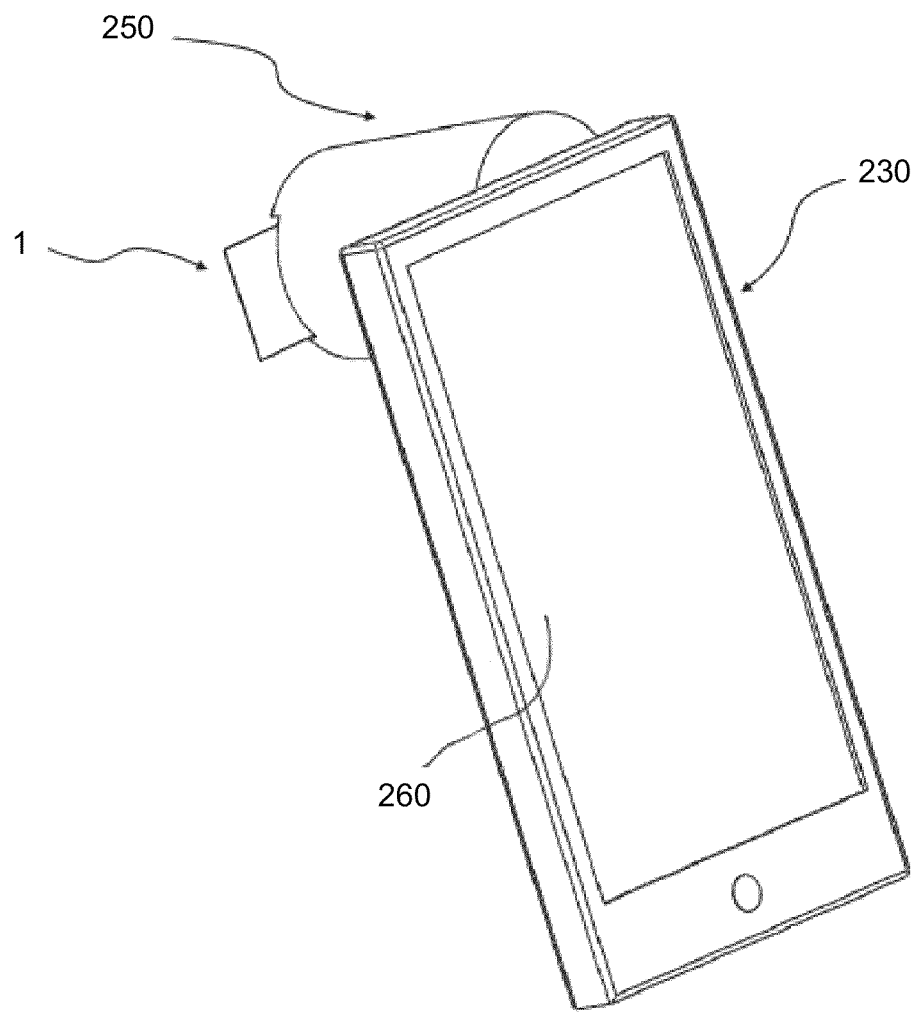
FIG. 15 is a block diagram illustrating a replica tape being secured to a holding component proximate to a camera of the exemplary apparatus illustrated in FIG. 14.

The mobile processing device 230 includes one or more processors (e.g., general purpose or application specific as discussed above with respect to FIG. 6), and a display device 260 (see FIG. 15). The display device may also function as an input unit in the case where the mobile processing device 230 has a touch-screen display for receiving user inputs. Alternatively, the mobile processing device 230 may have a separate input unit such as a keyboard and/or mouse for receiving a user input. The one or more processors of the mobile processing device 230 perform the functions of the image processor 205 as illustrated in FIG. 6, and the display unit of the mobile processing device 230 (as well as the aforementioned separate input unit in case the mobile processing device 230 does not include a touch-screen input unit) perform the functions of the operator interface processing unit 206 and display unit 205 illustrated in FIG. 6. The camera 240 of the mobile processing device 230 functions the image sensor 201 in the apparatus 100 of FIGS. 1 and 6 by measuring an intensity of the light respectively transmitted through at least two of the plurality of measurement points of the second surface of the replica tape 1. The mobile processing device 230 also includes a non-transitory computer-readable recording medium such as the MEM 626 illustrated in FIG. 6 having tangibly recorded thereon a computer program that causes the one or more processors of the mobile processing device 230 to carry out the features of the present disclosure.

Accordingly, in the apparatus 200 of FIG. 14, a replica tape 1 which has been embossed, compressed or cast on a surface of a material to replicate that surface is secured to the second surface of the holding component 250 as described above. The camera 240 of the mobile processing device 230, similar to the image sensor 201 in the apparatus 100, measures an intensity of light respectively transmitted through at least two of a plurality of measurement points of the second surface of the replica tape 1. The one or more processors of the mobile processing device 230, by executing the program recorded on the non-transitory computer-readable recording medium of the mobile processing device 230, may be configured to control and/or operate the camera 240 to measure the intensity of the light respectively transmitted through at least two measurement points of the second surface of the replica tape. For example, the one or more processors of the mobile processing device 230 may be configured to execute a specific computer program recorded in the memory unit to control the resident camera 204 to measure the intensity of the light transmitted through the at least two measurement points.

The one or more processors of the mobile processing device 230 are also configured to receive the measured intensity of the light transmitted through the at least two of the plurality of measurement points and convert the measured light intensity at the at least two measurement points into at least two data values each respectively relating to a measurement statistic of the replica tape 1 at a corresponding one of the at least two measurement points, respectively. Accordingly, the apparatus 200 illustrated in FIG. 14 is configured to perform all the operative functions and features of the above-described exemplary embodiments with the use of a mobile processing device 230 that is appropriately programmed to cause the one or more processors of the mobile processing device 230 to carry out the functions and features of the present disclosure, with a single holding component 250, as opposed to the first and second holding components 4, 5 in the exemplary apparatus 100 as illustrated in FIG. 1, for example.

FIG. 15 illustrates a representation of the back surface of the mobile processing device 230 (i.e., the surface of the mobile processing device having the camera 204 according to the example of FIG. 14) being applied (e.g., positioned proximate) to the first surface of the holding component 250, and the replica tape 1 being secured to the second surface of the holding component 250. In the example of FIG. 15, the front surface of the mobile processing device 230 includes a touch-screen display and input unit which is configured to output a visual and/or textual representation of the at least two data values each respectively relating to a measurement statistic of the replica tape at a corresponding one of the at least two measurement points, respectively.

In the exemplary apparatus 100 as described above, the inclusion of the first and second holding components 4, 5 provided a mechanism for the determination of the thickness of the replica tape 1, and the determined thickness of the replica tape 1 was used for determining a peak to valley thickness of the original surface replicated by the replica tape 1. In the exemplary apparatus 200 illustrated in FIGS. 14 and 15, the thickness of the replica tape, including the thickness of the backing 2, can be measured using a measurement device such as a spring loaded micrometer, and then this thickness measurement can be accounted for in converting the measured light intensity at two or more measurement points into at least two data values each respectively relating to a measurement statistic of the replica tape 1 at a corresponding one of the measurement points, in accordance with the features of the exemplary embodiments described above. For example, the measured thickness of the replica tape 1 can be input by a user into the mobile processing device 230 via the above-described input unit of the mobile processing device 230, and the one or more processors of the mobile processing device 230 can determine a peak to valley thickness of the measurement points of the replica tape 1 based on the measured intensity of the light intensity transmitted through the measurement points of the replica tape 1.

Figure 16:
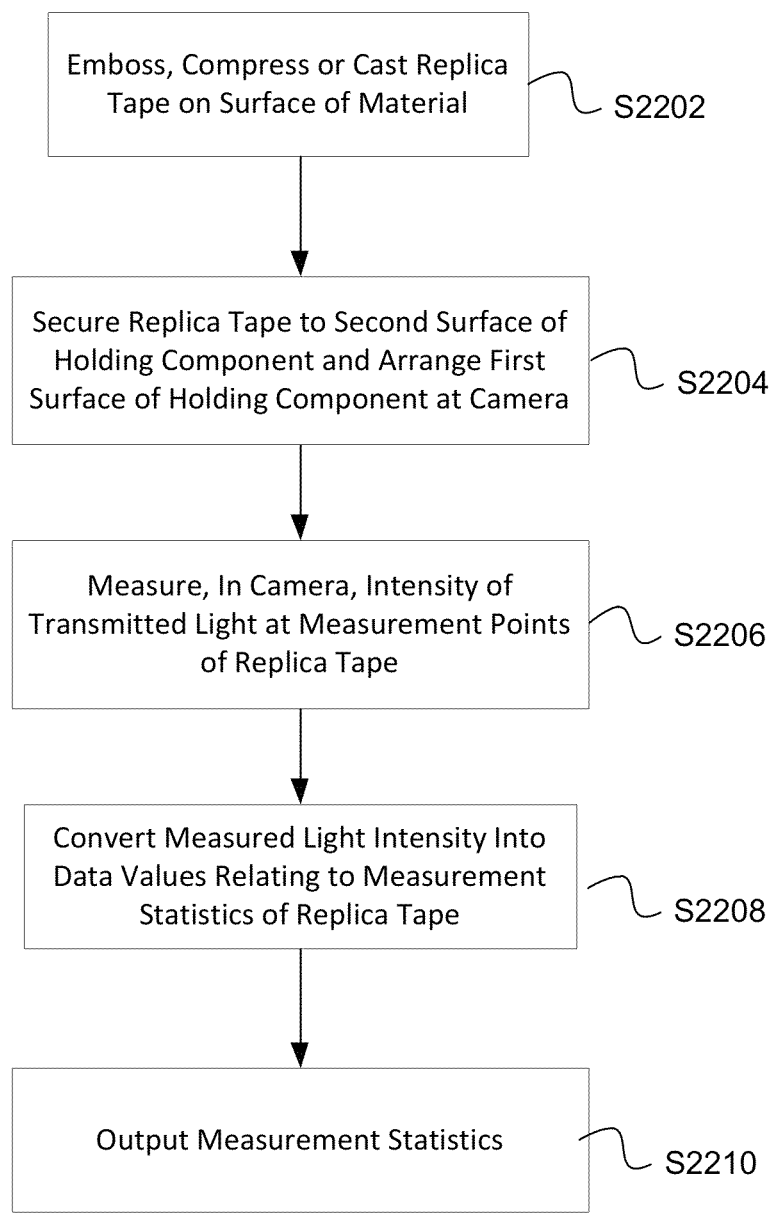
FIG. 16 is a flowchart illustrating steps of a method for characterizing a replica tape according to an exemplary embodiment of the present disclosure.

In accordance with the exemplary apparatus 200 described above, an exemplary embodiment of the present disclosure also provides a method for characterizing a surface of a material using a replica tape. FIG. 16 is a flowchart illustrating steps of an exemplary embodiment of the method according to the present disclosure. The exemplary method of the present disclosure includes embossing or compressing a replica tape on a surface of a material to be measured (S2202). The exemplary method also includes securing the first surface of the replica tape to the second surface of the holding component 250 so that the second surface of the replica tape 1 (e.g., the compressible surface) is directly exposed to light, and arranging the first surface of the holding component 250 at (e.g., proximate to) the camera 240 (S2204). As noted above, the light sequentially transmitted through the second and first surfaces of the replica tape 1 may be ambient light and/or light from an external light source. The exemplary method also includes measuring, in the camera 240 of the mobile processing device 230, an intensity of the light respectively transmitted through at least two measurement points of the compressible surface of the replica tape (S2206). The measurement of the intensity of the light transmitted through the at least two measurement points may include measuring a respective wavelength of the light transmitted through the at least two measurement points. Furthermore, the exemplary method includes converting, in the one or more processors of the mobile processing device 230, the measured light intensity transmitted through the at least two measurement points into at least two data values each respectively relating to a measurement statistic of the replica tape at a corresponding one of the at least two measurement points, respectively (S2208). The exemplary method may also include generating and displaying a 2 dimensional representation of the converted data values (S2210). The displayed representation may include, for example, an illustration of the characterized surface of the replica tape and/or an illustration of the surface of the replica tape. The exemplary method of the present disclosure may include any process steps in accordance with the operative features of the above-described apparatus 100 and 200.

In addition, an exemplary embodiment of the present disclosure provides a non-transitory computer-readable recording medium (e.g., a non-volatile memory such as a hard disk drive, ROM, or external memory such as flash memory) that is either resident in the mobile processing device 230 and/or external thereto, where the non-transitory computer-readable recording medium has tangibly recorded thereon a computer program that, when executed, causes one or more of the processors of the mobile processing device 230 to carry out the method of characterizing the surface of the replica tape in accordance with the above-described exemplary embodiments.

It will be appreciated by those skilled in the art that the present invention can be embodied in other specific forms without departing from the spirit or essential characteristics thereof. The presently disclosed embodiments are therefore considered in all respects to be illustrative and not restricted. The scope of the invention is indicated by the appended claims rather than the foregoing description and all changes that come within the meaning and range and equivalence thereof are intended to be embraced therein.

What is claimed is:

1. An apparatus for characterizing a replica tape which has been embossed, compressed or cast on a surface of a material, the replica tape including a first surface and an opposing second surface replicating the surface of the material on which the replica tape was embossed, compressed or cast, the second surface of the replica tape having a plurality of measurement points extending along a first direction substantially perpendicular to a thickness of the replica tape extending in a second direction between the first and second surfaces of the replica tape, wherein the apparatus comprises:
   a first holding component having opposing first and second surfaces in the second direction, the first surface of the first holding component being configured to support the second surface of the replica tape thereon;
   a second holding component having opposing first and second surfaces in the second direction, the second holding component being configured to be pressed against the first surface of the replica tape to secure the replica tape between the first surface of the first holding component and the second surface of the second holding component;
   a light source arranged a first distance from the first surface of the second holding component and configured to transmit light in the second direction through the first and second surfaces of the second holding component, the first and second surfaces of the replica tape, and the first and second surfaces of the first holding component;
   an image sensor arranged a second distance from the second surface of the first holding component and configured to measure an intensity of the light respectively transmitted through at least two of the plurality of measurement points of the second surface of the replica tape; and
   a processing unit configured to receive the measured intensity of the light transmitted through the at least two of the plurality measurement points and convert the measured light intensity at the at least two measurement points into at least two data values each respectively relating to a measurement statistic of the replica tape at a corresponding one of the at least two measurement points, respectively.

2. The apparatus according to claim 1, wherein the image sensor is configured to measure the intensity of the light respectively transmitted through the at least two measurement points by measuring an amplitude of a corresponding wavelength of the light transmitted through the at least two measurement points, respectively.

3. The apparatus according to claim 1, wherein the light source is configured to transmit light having a wavelength of 200 to 1500 nm.

4. The apparatus according to claim 1,
   wherein the light source is configured to transmit infrared light.

5. The apparatus according to claim 4, wherein the image sensor comprises a digital camera having a Bayer filter, and
   wherein the infrared light transmitted by the light source bypasses the Bayer filter of the digital camera.

6. The apparatus according to claim 4, comprising:
   a band pass filter arranged between the second surface of the first holding component and the image sensor, the band pass filter being configured to pass only infrared light to the image sensor.

7. The apparatus according to claim 1, comprising:
   an eddy current sensor arranged on the second surface of the first holding component;
   a conductive element attached to at least one point on a periphery of the second holding component between the first and second surfaces of the second holding component,
   wherein the second holding component and the conductive element attached to the second holding component are movable in the second direction,
   wherein the eddy current sensor is configured to measure a height of the conductive element above the first holding component, and
   wherein the processing unit is configured to measure a height of the second holding component based on the measured height of the conductive element, and convert the measured height of the second holding component to a peak to valley thickness according to the measured height of the second holding component.

8. The apparatus according to claim 1, wherein the replica tape includes a transparent backing attached to the first surface of the replica tape, and
   wherein the second holding component is configured to be pressed against the transparent backing to secure the replica tape between the first surface of the first holding component and the second surface of the second holding component.

9. The apparatus according to claim 8, wherein the backing is composed of one of polyester and nylon.

10. The apparatus according to claim 8, comprising:
    an eddy current sensor arranged on the second surface of the first holding component;
    a conductive element attached to at least one point on a periphery of the second holding component between the first and second surfaces of the second holding component,
    wherein the second holding component and the conductive element attached to the second holding component are movable in the second direction,
    wherein the eddy current sensor is configured to measure a height of the conductive element above the first holding component, and
    wherein the processing unit is configured to measure a height of the second holding component based on the measured height of the conductive element, and convert the measured height of the second holding component to a peak to valley thickness by subtracting the measured height of the second holding component from a thickness of the transparent backing.

11. The apparatus according to claim 8, comprising:
an eddy current sensor arranged on the second surface of the first holding component,
wherein the second holding component is composed of a conductive material and is moveable in the second direction,
wherein the eddy current sensor is configured to measure a height of the second holding component above the first holding component, and
wherein the processing unit is configured to convert the measured height of the second holding component to a peak to valley thickness by subtracting the measured height of the second holding component from a thickness of the transparent backing.

12. The apparatus according to claim 1, comprising:
an eddy current sensor arranged on the second surface of the first holding component,
wherein the second holding component is composed of a conductive material and is moveable in the second direction,
wherein the eddy current sensor is configured to measure a height of the second holding component above the first holding component, and
wherein the processing unit is configured to convert the measured height of the second holding component to a peak to valley thickness according to the measured height of the second holding component.

13. The apparatus according to claim 1, comprising:
a first spring configured to apply a first predetermined force to the first surface of the second holding component to keep pressure between the second holding component and the replica tape constant, regardless of operator input.

14. The apparatus according to claim 11, comprising:
a second spring surrounding the second holding component;
a first ring surrounding the second holding component and having an inner groove configured to accommodate and engage the second spring between the first and second surfaces of the second holding component, and an outer tapered surface; and
a pair of buttons respectively disposed on opposite sides of the second holding component and each including an inner tapered surface matching a contour of the outer tapered surface of the first ring,
wherein the pair of buttons are configured to be depressed to become engaged with the first ring and compress the first ring toward the first holding component such that the second holding component is held in place only by means of the first spring, and to release the pressure between the second holding component and the replica tape from the first spring by applying a second predetermined force, which is greater than the first predetermined force, against the first spring to retract the first spring away from the first holding component.

15. The apparatus according to claim 14, comprising:
a second ring affixed to at least one point along a periphery of the second holding component between the first and second surfaces of the second holding component,
wherein the second spring is arranged above the second ring in the second direction.

16. The apparatus according to claim 1, wherein the processing unit is configured to record in a memory unit the received measured light intensity at the at least two measurement points, and convert the measured light intensity at the at least two measurement points by substituting the recorded measured light intensity with thickness values recorded in a look-up table in association with corresponding values of the measured light intensity, respectively.

17. The apparatus according to claim 16, comprising:
an operator interface processing unit configured to receive an operator input to update the thickness values recorded in the look-up table.

18. The apparatus according to claim 17, wherein the operator interface processing unit is configured to receive an update to the thickness values based on a linearization of a response function for the replica tape.

19. The apparatus according to claim 16, comprising:
a display unit configured to display at least one of: (i) a two-dimensional rendering of the thickness values corresponding to the measured light intensity at the at least two measurement points, and (ii) a two-dimensional rendering of a three-dimensional surface of the replica tape based on the thickness values corresponding to the measured light intensity at the at least two measurement points.

20. The apparatus according to claim 19, wherein the processing unit is configured to generate an image in which a portion of the replica tape having the maximum thickness of the replica tape is correlated with a darkest area of the image to correct for variations between samples of the replica tape.

21. The apparatus according to claim 16, wherein the look-up table is based on measured thickness values of the replica tape in association with corresponding measured light intensities that are stored after calibration with measured thickness values of an uncompressed, unembossed or uncast replica tape in association with corresponding measured light intensities of the uncompressed, unembossed or uncast replica tape.

22. The apparatus according to claim 16, wherein the look-up table is based on measured thickness values recorded without being associated with measured light intensities of measurement points of the replica tape to account for at least one of (i) variations in measurements, (ii) changes to mechanical components of the apparatus, and (iii) buildup of debris in the apparatus.

23. The apparatus according to claim 1, wherein the processing unit is configured to record in a memory unit the received measured light intensity at the at least two measurement points, and convert the measured light intensity at the at least two measurement points by applying an algorithm to the recorded measured light intensity to obtain corresponding thickness values for the measured light intensity at the at least two measurement points, respectively.

24. The apparatus according to claim 23, comprising:
an operator interface processing unit configured to receive an operator input to update the thickness values recorded in the look-up table.

25. The apparatus according to claim 24, wherein the operator interface processing unit is configured to receive an update to the thickness values based on a linearization of a response function for the replica tape.

26. The apparatus according to claim 23, comprising:
a display unit configured to display at least one of: (i) a two-dimensional rendering of the thickness values corresponding to the measured light intensity at the at least two measurement points, and (ii) a two-dimensional rendering of a three-dimensional surface of the replica tape based on the thickness values corresponding to the measured light intensity at the at least two measurement points.

27. The apparatus according to claim 26, wherein the processing unit is configured to generate an image in which a portion of the replica tape having the maximum thickness of the replica tape is correlated with a darkest area of the image to correct for variations between samples of the replica tape.

28. The apparatus according to claim 23, wherein the algorithm is based on measured thickness values of the replica tape in association with corresponding measured light intensities that are recorded after calibration with measured thickness values of an uncompressed, unembossed or uncast replica tape in association with corresponding measured light intensities of the uncompressed, unembossed or uncast replica tape.

29. The apparatus according to claim 23, wherein the algorithm is based on measured thickness values recorded without being associated with measured light intensities of measurement points of the replica tape to account for at least one of (i) variations in measurements, (ii) changes to mechanical components of the apparatus, and (iii) buildup of debris in the apparatus.

30. The apparatus according to claim 1, wherein the processing unit is configured to determine at least one marking in the replica tape to distinguish between different grades of the replica tape, and adjust corresponding thickness values associated with the measured light intensities at the at least two measurement points based on a particular grade of the replica tape.

31. The apparatus according to claim 1, wherein the first holding component includes a transparent window, and the second holding component includes a translucent anvil.

32. The apparatus according to claim 1, wherein the first and second holding components are each respectively comprised of a support structure for supporting the replica tape therebetween and one of a window and a hole arranged in the corresponding support structure to enable light from the light source to be transmitted therethrough.

33. A method for characterizing a replica tape, the method comprising:
  embossing, compressing or casting the replica tape on a surface of a material to be measured, the embossed, compressed or cast replica tape having a compressible surface which replicates the surface of the material;
  securing the replica tape between a first holding component and a second holding component such that the compressible surface of the replica tape is secured against the first holding component;
  transmitting light through the second holding component, the replica tape and the first holding component;
  measuring, in an image sensor, an intensity of the light respectively transmitted through at least two measurement points of the compressible surface of the replica tape; and
  converting, in a processing unit, the measured light intensity transmitted through the at least two measurement points into at least two data values each respectively relating to a measurement statistic of the replica tape at a corresponding one of the at least two measurement points, respectively.

34. The method according to claim 33, comprising:
  generating and displaying a two-dimensional representation of the converted data values,
  wherein the generated and displayed two-dimensional representation of the converted data values includes at least one of: (i) a two-dimensional rendering of thickness values of the replica tape corresponding to the measured light intensity at the at least two measurement points, and (ii) a two-dimensional rendering of a three-dimensional surface of the replica tape based on the thickness values corresponding to the measured light intensity at the at least two measurement points.

35. The method according to claim 34, wherein the generating and displaying of the two-dimensional representation of the converted data values includes generating an image in which a portion of the replica tape having the maximum thickness of the replica tape is correlated with a darkest area of the image to correct for variations between samples of the replica tape.

36. The method according to claim 33, wherein a conductive element is attached to at least one point on a periphery of the second holding component between opposing surfaces of the second holding component,
  wherein the second holding component and the conductive element attached to the second holding component are movable in a direction of the thickness of the replica tape, and
  wherein the method comprises:
  measuring a height of the conductive element above the first holding component;
  measuring a height of the second holding component based on the measured height of the conductive element; and
  converting the measured height of the second holding component to a peak to valley thickness according to the measured height of the second holding component.

37. The method according to claim 33, wherein the replica tape includes a transparent backing attached to the first surface of the replica tape,
  wherein the second holding component is pressable against the transparent backing to secure the replica tape between the first and second holding components,
  wherein a conductive element is attached to at least one point on a periphery of the second holding component between opposing surfaces of the second holding component,
  wherein the second holding component and the conductive element attached to the second holding component are movable in a direction of the thickness of the replica tape, and
  wherein the method comprises:
  measuring a height of the conductive element above the first holding component;
  measuring a height of the second holding component based on the measured height of the conductive element; and
  converting the measured height of the second holding component to a peak to valley thickness by subtracting the measured height of the second holding component from a thickness of the transparent backing.

38. The method according to claim 33, wherein the converting of the measured light intensity comprises:
  recording in a memory unit the received measured light intensity at the at least two measurement points; and
  converting the measured light intensity at the at least two measurement points by substituting the recorded measured light intensity with thickness values recorded in a look-up table in association with corresponding values of the measured light intensity, respectively.

39. The method according to claim 38, wherein the look-up table is based on measured thickness values of the replica tape in association with corresponding measured light intensities that are stored after calibration with measured thickness values of an uncompressed, unembossed or uncast replica tape in association with corresponding measured light intensities of the uncompressed, unembossed or uncast replica tape.

40. The method according to claim 33, wherein the converting of the measured light intensity comprises:

recording in a memory unit the received measured light intensity at the at least two measurement points; and converting the measured light intensity at the at least two measurement points by applying an algorithm to the recorded measured light intensity to obtain corresponding thickness values for the measured light intensity at the at least two measurement points, respectively.

41. The method according to claim 40, wherein the algorithm is based on measured thickness values of the replica tape in association with corresponding measured light intensities that are recorded after calibration with measured thickness values of an uncompressed, unembossed or uncast replica tape in association with corresponding measured light intensities of the uncompressed, unembossed or uncast replica tape.

* * * * *